United States Patent
Sauer

(10) Patent No.: US 11,229,441 B2
(45) Date of Patent: Jan. 25, 2022

(54) MINIMALLY INVASIVE SURGICAL CLAMPING DEVICE AND METHODS THEREOF

(71) Applicant: LSI Solutions, Inc., Victor, NY (US)

(72) Inventor: Jude S. Sauer, Pittsford, NY (US)

(73) Assignee: LSI SOLUTIONS, INC., Victor, NY (US)

(*) Notice: Subject to any disclaimer, the term of this patent is extended or adjusted under 35 U.S.C. 154(b) by 62 days.

(21) Appl. No.: 16/592,898

(22) Filed: Oct. 4, 2019

(65) Prior Publication Data

US 2020/0107835 A1 Apr. 9, 2020

Related U.S. Application Data

(60) Provisional application No. 62/741,329, filed on Oct. 4, 2018.

(51) Int. Cl.
| | | |
|---|---|---|
| *A61B 17/128* | (2006.01) | |
| *A61B 17/04* | (2006.01) | |
| (Continued) | | |

(52) U.S. Cl.
CPC ...... *A61B 17/1285* (2013.01); *A61B 17/0466* (2013.01); *A61L 31/128* (2013.01);
(Continued)

(58) Field of Classification Search
CPC ............ A61B 17/0466; A61B 17/0483; A61B 17/06166; A61B 17/06195; A61B 17/122;
(Continued)

(56) References Cited

U.S. PATENT DOCUMENTS

| | | |
|---|---|---|
| 3,581,551 A | 6/1971 | Wilkinson |
| 4,016,883 A | 4/1977 | Wright |
| (Continued) | | |

FOREIGN PATENT DOCUMENTS

| | | |
|---|---|---|
| EP | 0615724 | 6/1998 |
| EP | 1654992 | 1/2008 |

OTHER PUBLICATIONS

Jan. 29, 2016 Office Action; Rwego, Kankindi.
Jan. 1, 2013 Cygnet Flexible Clamps, Copyright 2003; Vitalitec, Product Literature.

*Primary Examiner* — Brooke Nicole Labranche
(74) *Attorney, Agent, or Firm* — Michael E. Cayne; Christopher B. Miller

(57) ABSTRACT

A surgical clamping device is disclosed, having a first clamp jaw and a second clamp jaw, each having one or more channels configured for receiving suture for reliably securing the clamp jaws to maintain a clamping pressure during a surgical procedure, as well as to reliably and releasably secure the clamp jaws onto the introducer shaft of the clamping device. Also described are clamp jaws having one or more actuator interfaces and alignment guides configured for reversible and slidable engagement with an actuator at the end of an articulating introducer shaft. Also described are various features of clamp jaws for use with a surgical clamping device. Also disclosed is a surgical clamping device having detachable, pivotable first and second clamp jaws releasably held on pivotable fingers at a proximal end of an articulating introducer shaft. Related methods of surgical clamping procedures are also disclosed.

14 Claims, 33 Drawing Sheets

(51) Int. Cl.
*A61L 31/12* (2006.01)
*A61B 17/00* (2006.01)
*A61B 17/29* (2006.01)

(52) U.S. Cl.
CPC ........... *A61B 2017/00243* (2013.01); *A61B 2017/00424* (2013.01); *A61B 2017/00473* (2013.01); *A61B 2017/00862* (2013.01); *A61B 2017/2902* (2013.01); *A61B 2017/2925* (2013.01); *A61B 2017/2927* (2013.01)

(58) Field of Classification Search
CPC ...... A61B 17/1285; A61B 2017/00243; A61B 2017/00424; A61B 2017/00473; A61B 2017/0086; A61B 2017/0496; A61B 2017/2902; A61B 2017/2923; A61B 2017/2925; A61B 2017/2927; A61B 2017/2934; A61B 2017/2936; A61B 2017/294; A61B 17/128; A61B 17/08; A61B 17/10; A61B 2017/2931; A61L 31/128
See application file for complete search history.

(56) References Cited

U.S. PATENT DOCUMENTS

| | | | |
|---|---|---|---|
| 4,997,436 | A | 3/1991 | Oberlander |
| 5,133,724 | A | 7/1992 | Wilson |
| 5,514,148 | A | 5/1996 | Smith |
| 5,618,307 | A | 4/1997 | Donlon |
| 5,716,370 | A | 2/1998 | Williamson |
| 5,776,146 | A | 7/1998 | Sackier |
| 5,797,959 | A | 8/1998 | Castro |
| 5,855,590 | A | 1/1999 | Malecki |
| 5,921,996 | A | 7/1999 | Sherman |
| 5,964,780 | A | 10/1999 | Balazs |
| 6,036,706 | A | 3/2000 | Morejohn |
| 6,146,394 | A | 11/2000 | Morejohn |
| 6,293,954 | B1* | 9/2001 | Fogarty ............... A61B 17/282 606/151 |
| 6,368,340 | B2 | 4/2002 | Malecki |
| 6,610,074 | B2 | 8/2003 | Santilli |
| 6,926,712 | B2 | 8/2005 | Phan |
| 6,942,676 | B2 | 9/2005 | Buelna |
| 7,108,703 | B2 | 9/2006 | Danitz |
| 7,455,678 | B2 | 11/2008 | Santilli |
| 7,901,418 | B2* | 3/2011 | Danitz ............... A61B 17/122 606/157 |
| 7,951,147 | B2 | 5/2011 | Privitera |
| 7,963,964 | B2 | 6/2011 | Santilli |
| 7,997,468 | B2 | 8/2011 | Farascioni |
| 8,303,611 | B2 | 11/2012 | Danitz |
| 8,409,229 | B2 | 4/2013 | Wiedenbein |
| 8,529,585 | B2 | 9/2013 | Jacobs |
| 2005/0165429 | A1 | 7/2005 | Douglas |
| 2006/0028041 | A1 | 2/2006 | Ono et al. |
| 2007/0213747 | A1* | 9/2007 | Monassevitch .... A61B 17/0643 606/151 |
| 2009/0209986 | A1 | 8/2009 | Stewart |
| 2010/0063538 | A1 | 3/2010 | Spivey |
| 2011/0039967 | A1 | 2/2011 | Wilson et al. |
| 2011/0288579 | A1 | 11/2011 | Hyodo |
| 2012/0037686 | A1 | 2/2012 | Hessler |
| 2012/0245598 | A1 | 9/2012 | Brown |
| 2015/0018856 | A1 | 1/2015 | Poo |
| 2016/0310120 | A1* | 10/2016 | Swift ............... A61B 90/30 |

* cited by examiner

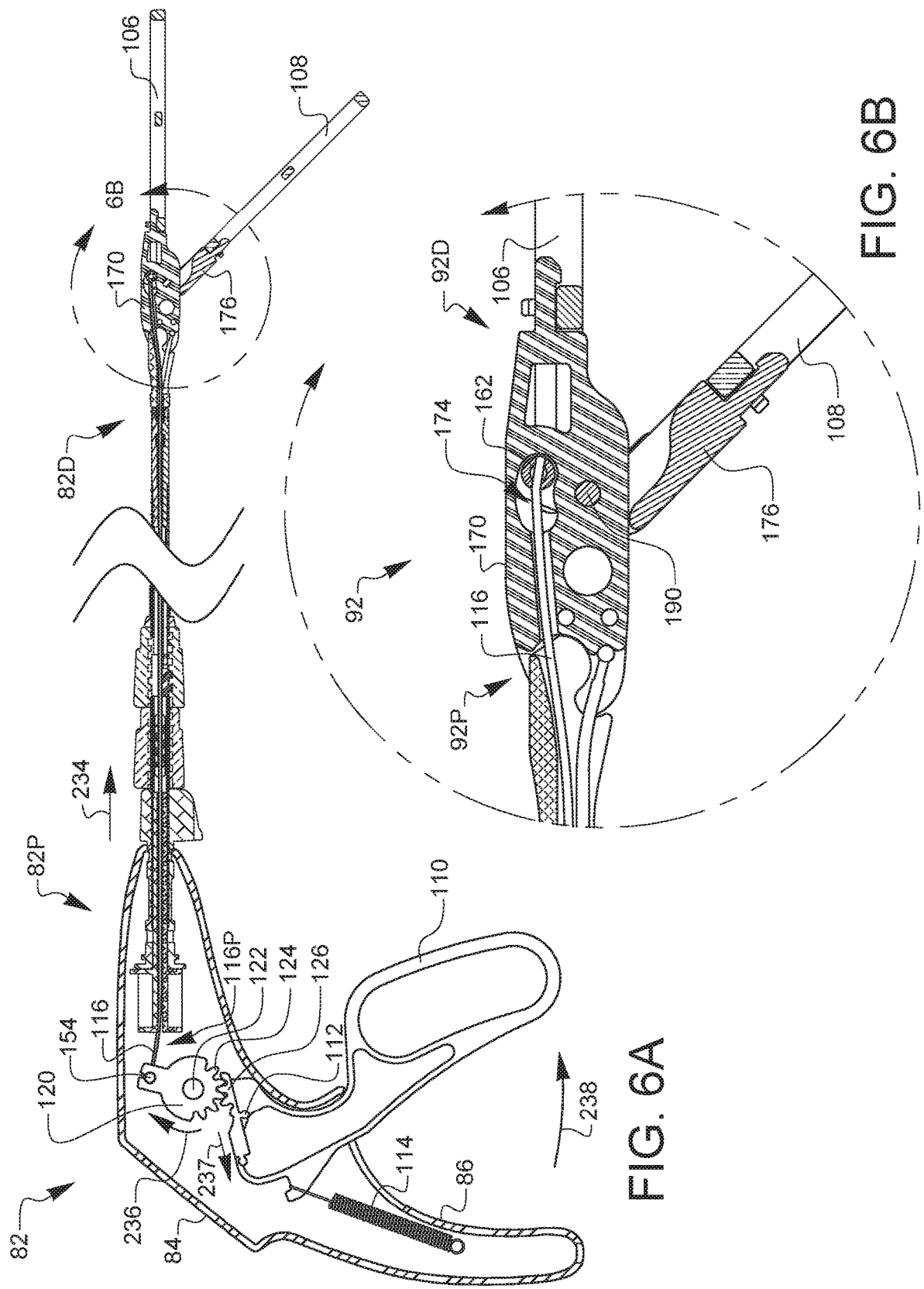

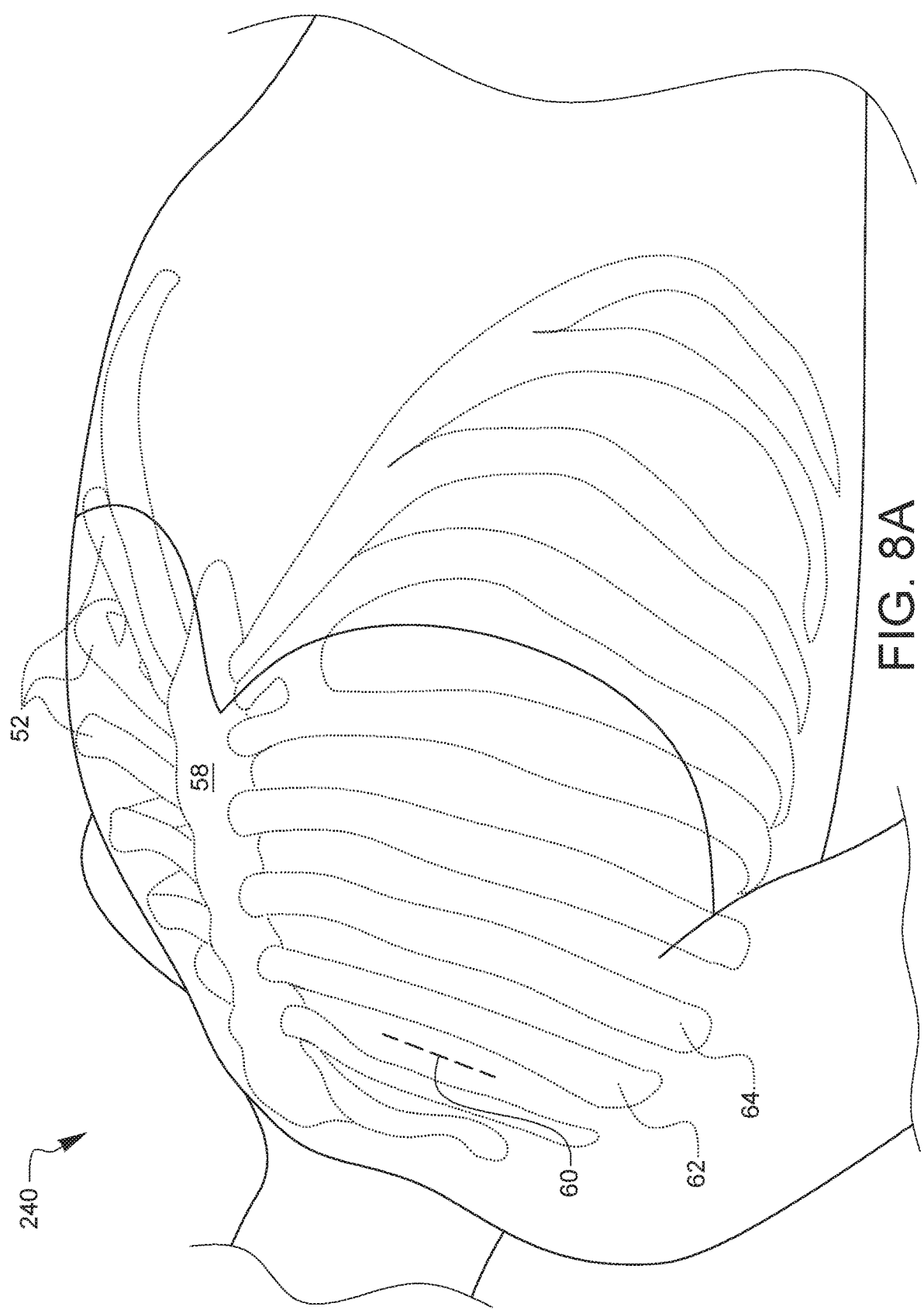

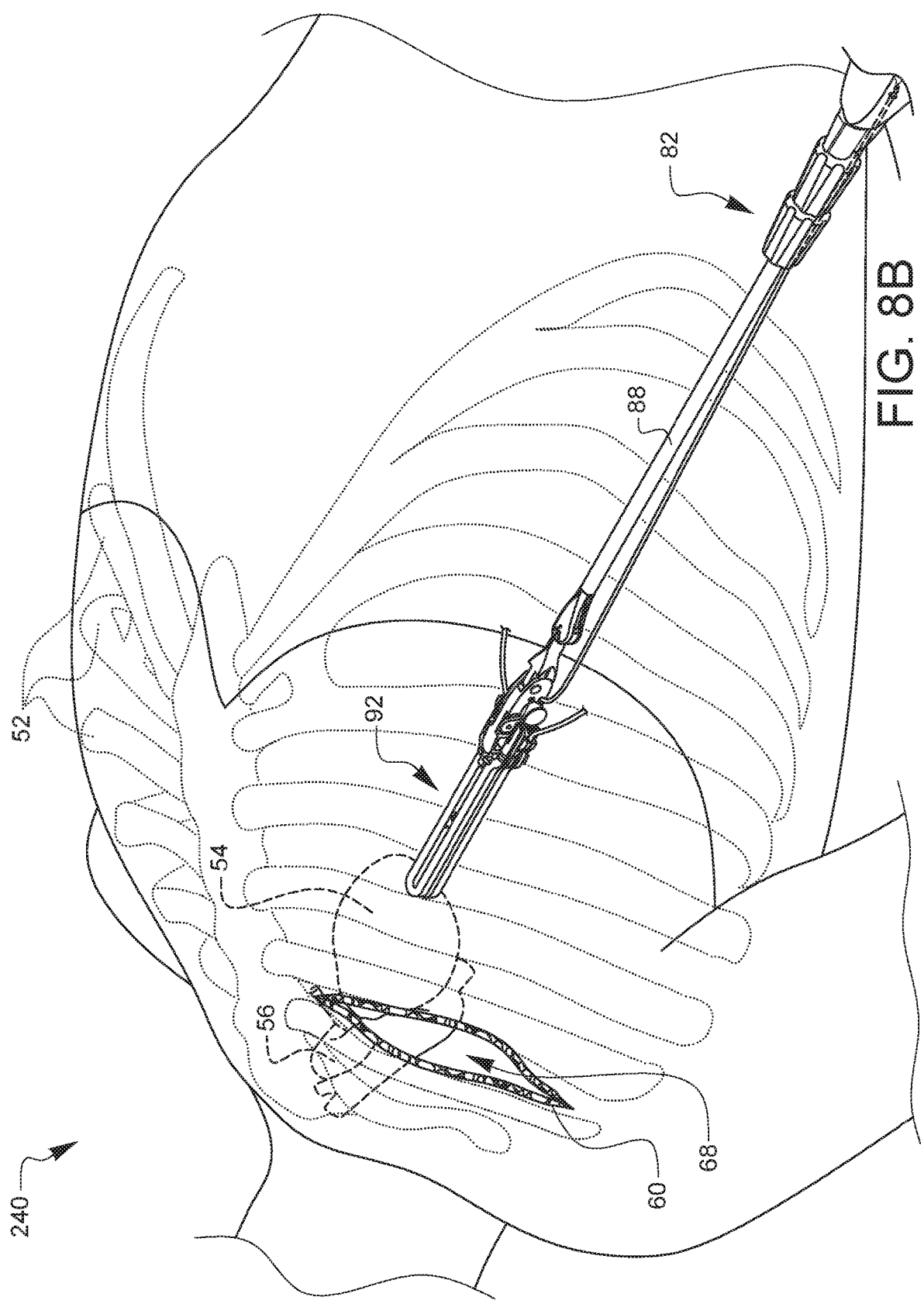

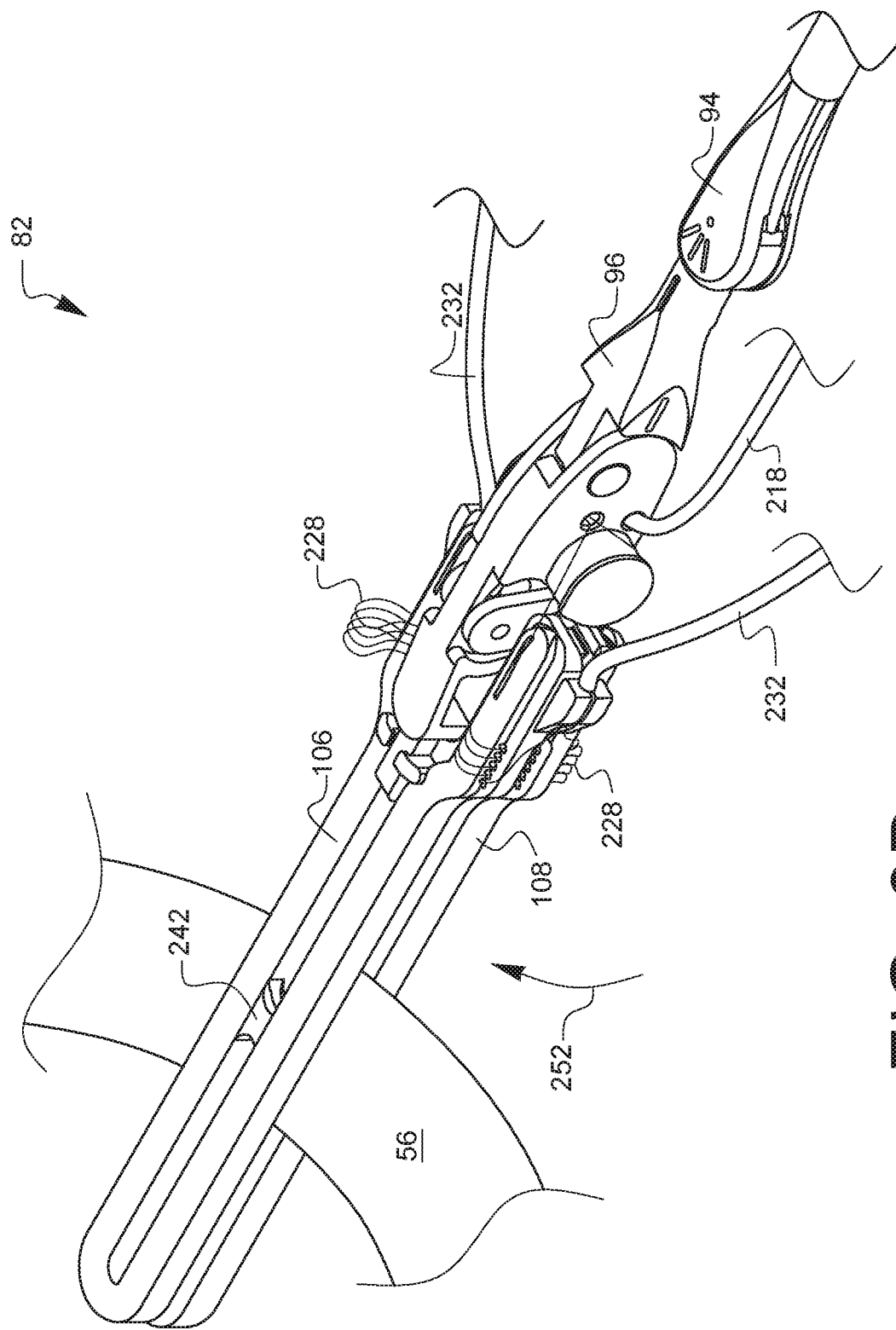

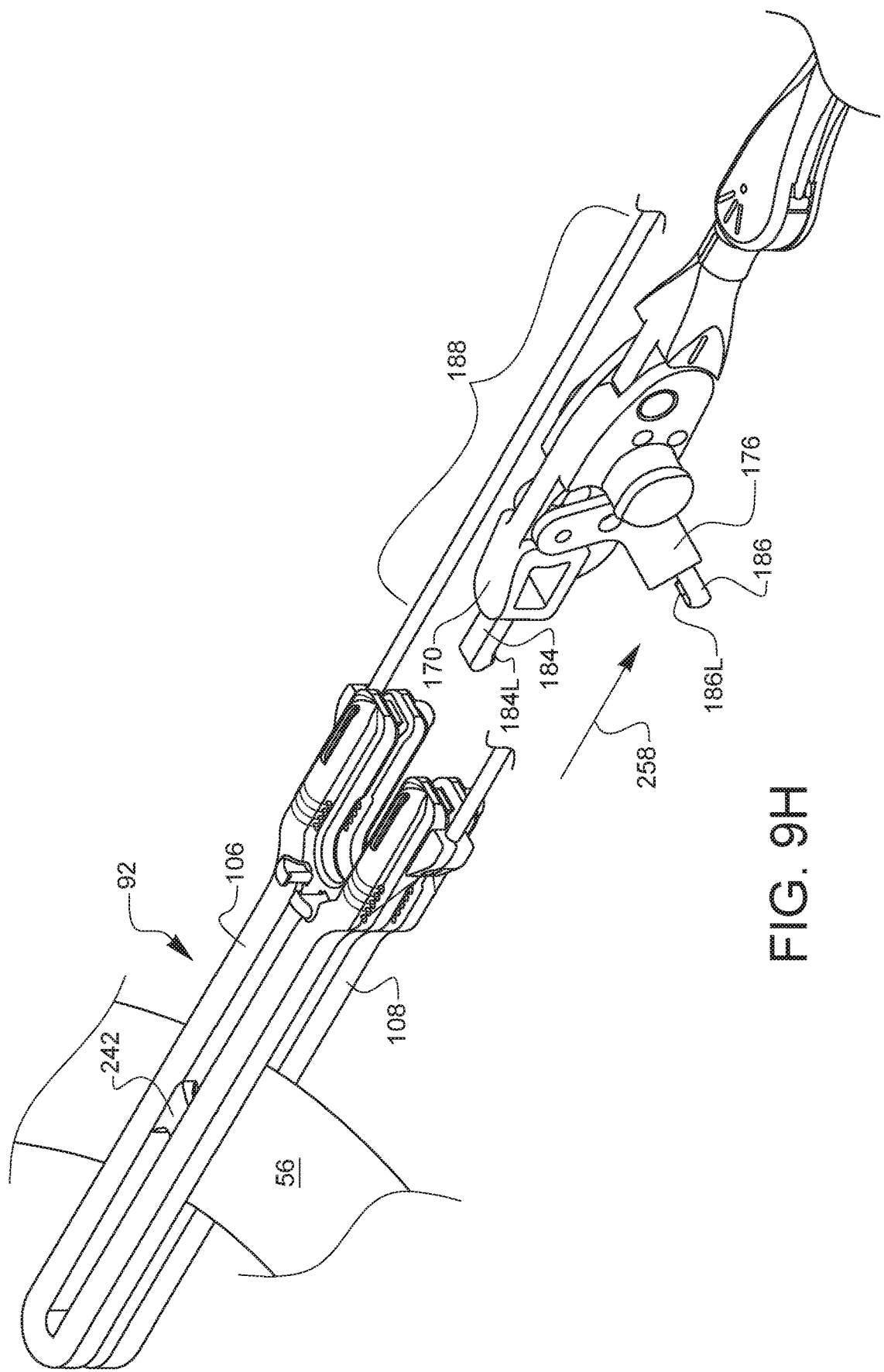

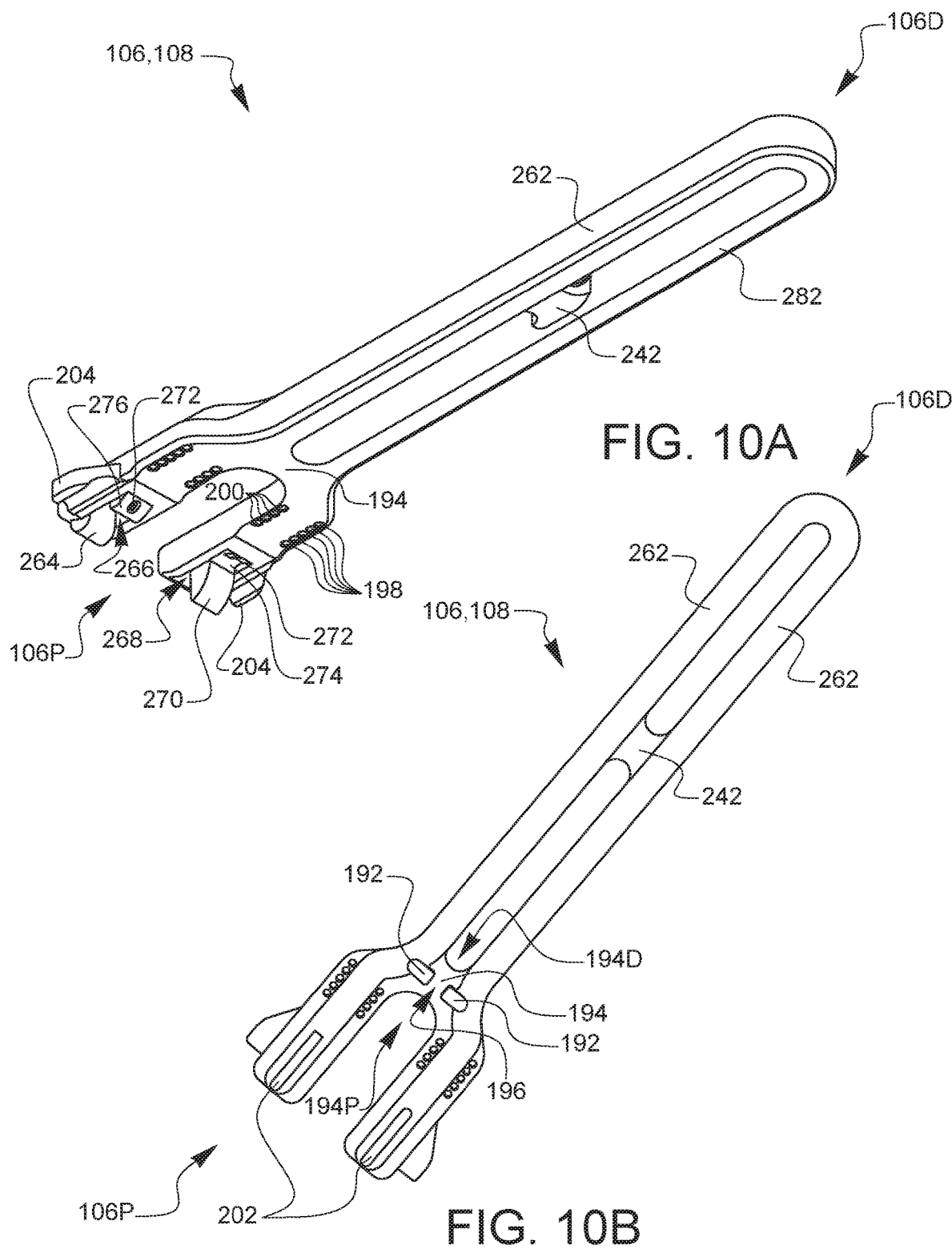

MINIMALLY INVASIVE SURGICAL CLAMPING DEVICE AND METHODS THEREOF

REFERENCE TO RELATED APPLICATION

This patent application claims priority to U.S. Provisional Patent Application No. 62/741,329 filed Oct. 4, 2018 and entitled "SURGICAL CLAMPING DEVICE AND METHODS THEREOF." The 62/741,329 application is hereby incorporated by reference in its entirety.

FIELD

The claimed invention relates to clamping devices, and more specifically to a surgical clamping device.

BACKGROUND

The ability of cardiac surgeons to successfully treat an ever-increasing number of heart conditions is well-documented. From relatively crude attempts by surgeons to repair stab wounds to the heart at start of the $20^{th}$ century, to exploratory attempts in the first half of the 1900's to open or repair heart valves before reliable cardio-pulmonary bypass (CPB) became available, to the steady stream of advances in cardiology in the second half of the $20^{th}$ century, including CPB improvements and cold blood cardioplegia techniques to enable increased operating time while minimizing damage to the heart, prosthetic heart valve development for mitral and aortic valve replacement, coronary artery bypass grafting, and a host of other cardiac procedures, open heart surgery continues to improve at an impressive rate. As the $21^{st}$ century is well underway, cardiac surgery continues to improve, with a focus on less invasive heart surgery.

A variety of technologies, knowledge, and surgical skills are utilized to enable less invasive cardiac surgery. As one example, consider one method of aortic valve replacement and the logistical situation presented by such a surgery as highlighted in FIGS. 1 and 2. FIG. 1 schematically illustrates a human thorax 50 outlined in a solid line with ribcage 52 approximated with the broken lines. A heart 54 and some of the veins and arteries leading to and from the heart 54 are represented by the dotted lines. The heart 54, and in particular, the aorta 56 are generally well protected by the ribcage 52. Before recent advances in cardiac surgery, it was frequently necessary to "crack" the sternum 58 and spread the left and right halves of the ribcage 52 following a sternotomy (incision which can run twenty centimeters (cm) or more down a patient's chest over the sternum 58). However, while providing excellent access to the heart 54 it is preferable to avoid a sternotomy and the long recovery times and high levels of pain associated with such invasive surgery.

As a less invasive alternative, surgeons are often able to use a thoracotomy (preferably an incision between the ribs) as an access point to operate on the heart. FIG. 2 schematically illustrates a thoracotomy in the context of this aortic valve replacement example. A minimally invasive incision 60 is made in the right second intercostal space (between the second and third ribs 62, 64) while simultaneously gaining percutaneous access to a femoral vein 66. Muscle is dissected from the ribs 62, 64 and retractors (not shown) are placed to spread the incision 60 and the ribs 62, 64 to create a minimally invasive opening 68. With access available through a less invasive opening 68, the pericardium is incised over the aorta 56. Stay sutures (not shown) can be placed in tissues and pulled back to increase access to the aorta 56.

A venous cannula 70 is prepared and inserted after dilation of the percutaneous incision in the femoral vein 66. A guide wire can be placed into the venous cannula 70 and threaded through the femoral vein 66, through the inferior vena cava 72, into the right atrium 74 of the heart 54, and into the superior vena cava 76. A series of dilators (not shown) are used to widen the guide wire tract to the venous cannula 70. The venous cannula 70 is attached to the input side of a CPB machine 78, providing a path for the bypass machine 78 to grab deoxygenated blood that has returned from the body to the heart 54. An aortic cannula 80 is also placed and attached to the output side of the bypass machine 78, providing a place for re-oxygenated blood (supplied by the bypass machine 78) to be returned to the body.

The superior vena cava 76 is dissected away from the aorta 56, and an aortic cross clamp (not shown) is introduced on the heart side of the aortic cannula 80, but away from the aortic valve. The aortic cross clamp seals the aorta 56 so that the CPB machine 78 can begin circulating oxygenated blood to the body without leakage back through the heart 54. The heart 54 is stopped, for example, by medication and/or lowering the temperature of the heart, and a transverse aortotomy is created to expose the aortic valve. The defective aortic valve is then cut out and care is taken to remove any debris, such as calcium or plaque deposits, which may have accumulated on the valve and come loose during the valve removal.

A replacement aortic valve (either mechanical, synthetic, or donor tissue) is then seated and sewed into place. The aortotomy is then closed. The aortic cross clamp is removed, the heart 54 is restarted, and the cannula connection points 70, 80 are removed to disconnect the patient from the CPB machine 78. Finally, the remaining open incisions are closed.

While the minimally invasive nature of the incisions can result in shortened patient recovery times, the demands on a surgeon during such a procedure can be high considering that the surgeon has a very small incision window defined by the opening 68 within which the operation must take place. Space is at a premium, and the surgeon must find a way to manage tubing for the aortic cannula and associated tubing for the CPB machine, the aortic cross-clamp, pull-back sutures, closure sutures for the cannula incision, and any of the necessary scalpels, manipulators, suture needles, and suction devices so that there is still room to install the replacement valve through the opening 68 in the ribs.

If an aortic cross clamp inappropriately releases or slips off the aorta, visualization and hemodynamic control can be lost, and the patient can exsanguinate. Therefore, there is first and foremost a need for surgical clamp devices that have a reliable and strong clamping force. There is also a need for such surgical clamping devices to be compatible with less invasive cardiac surgical procedures such that surgeons can easily operate and manipulate the clamps through small access sites, such as a port or a cannula, or through a small incision while preferably creating little to no reduction in the surgical access area. There is further a need for such surgical clamps to be easily releasable and removable.

SUMMARY

A surgical device is disclosed. The surgical device includes a first clamp jaw and a second clamp jaw, each including one or more channels one or more actuator interfaces and one or more alignment guides.

Another surgical device is disclosed. The surgical device includes a first clamp jaw and a second clamp jaw, each including one or more channels, one or more actuator interfaces, and one or more alignment guides, where the one or more channels are configured for receiving one or more sutures, where the one or more sutures are configured to be secured with a mechanical fastener to maintain a clamping pressure, and where at least one of the first and second clamp jaw is pivotable relative to the other. The surgical device also includes an actuator configured for slidable engagement in contact with an actuator interface on at least one or more of the first and second clamp jaws, and where a suture used for holding the first and second clamp jaws onto an actuator is configured to be secured with a fastener.

A method of using a surgical device for tissue clamping is disclosed. This method of surgical tissue clamping, includes creating an incision in an intercostal space in a patient, introducing a distal end of a surgical clamping device into the incision, closing a first clamp jaw and a second clamp jaw around a blood vessel such that blood flow through a vessel is restricted during a minimally invasive surgical procedure. The method of tissue clamping also includes disengaging an actuator of the surgical clamping device from the first clamp jaw and the second clamp jaw for the duration of the minimally invasive surgical procedure.

BRIEF DESCRIPTION OF THE DRAWINGS

FIGS. 6A and 7A are partial cross-sectional side views illustrating the opened and closed positions, respectively, of the minimally invasive surgical clamping device of FIG. 3A.

FIGS. 6B and 7B are enlarged views of FIGS. 4A and 5A, respectively, showing the clamping end in more detail.

FIG. 8A is a perspective view of a chest area of a patient undergoing a surgical procedure.

FIG. 8B is a perspective view of the patient of FIG. 8A and the minimally invasive surgical clamping device of FIG. 3A in the closed position.

FIG. 9B is a perspective view of the surgical clamping device of FIG. 3A from inside a body cavity in a clamped or closed position.

FIG. 9H is a perspective view of the surgical clamping device of FIG. 3A in a separated and locked and clamped or closed position.

FIG. 10A is a bottom-right perspective view of a clamping jaw of the surgical clamping device of FIG. 3A.

FIG. 10B is a top-right perspective view of a clamping jaw of the surgical clamping device of FIG. 3A.

DETAILED DESCRIPTION

Figure 1:
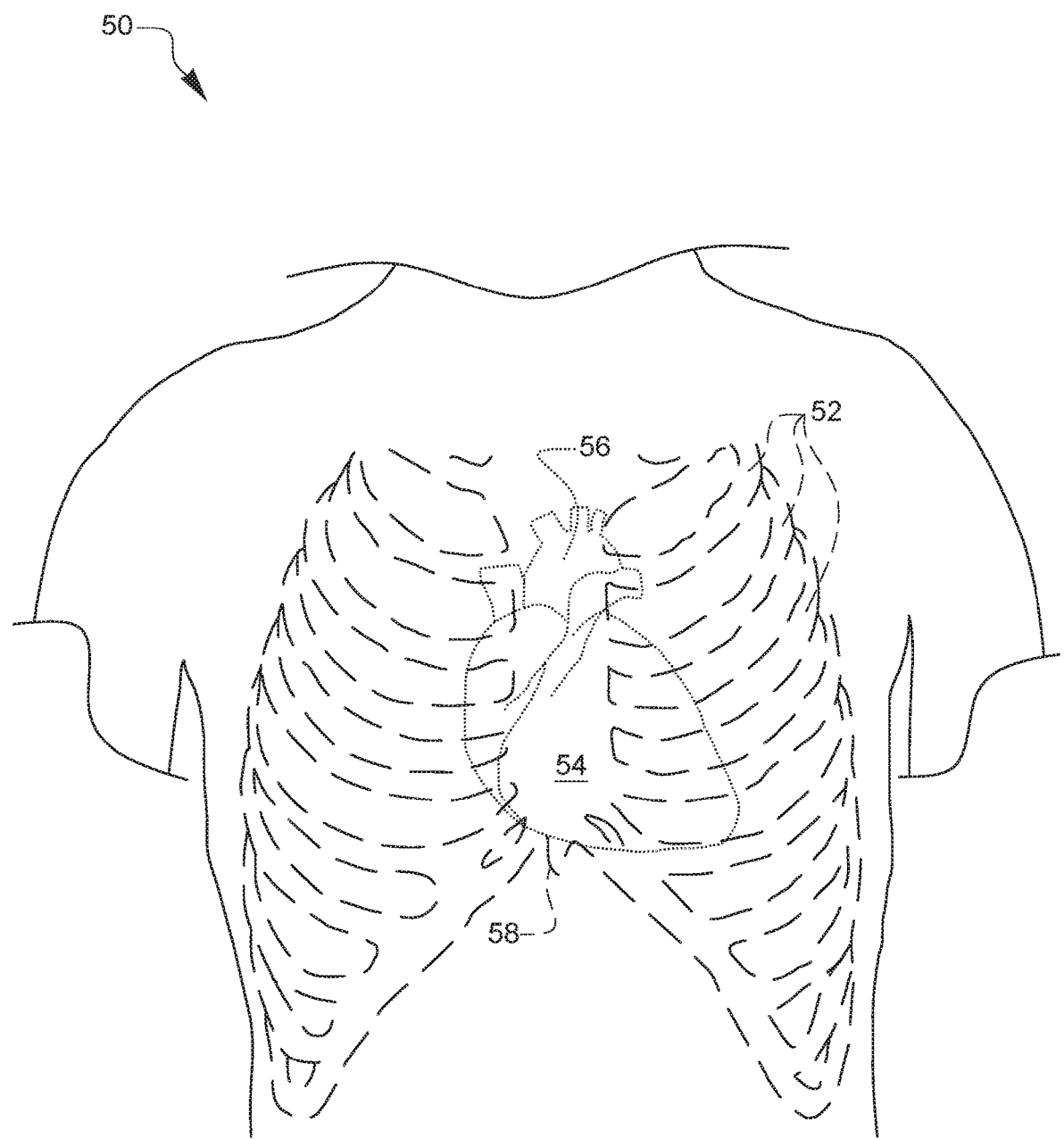
FIG. 1 schematically illustrates the relative locations of the heart and ribcage in a human thorax.
Figure 2:
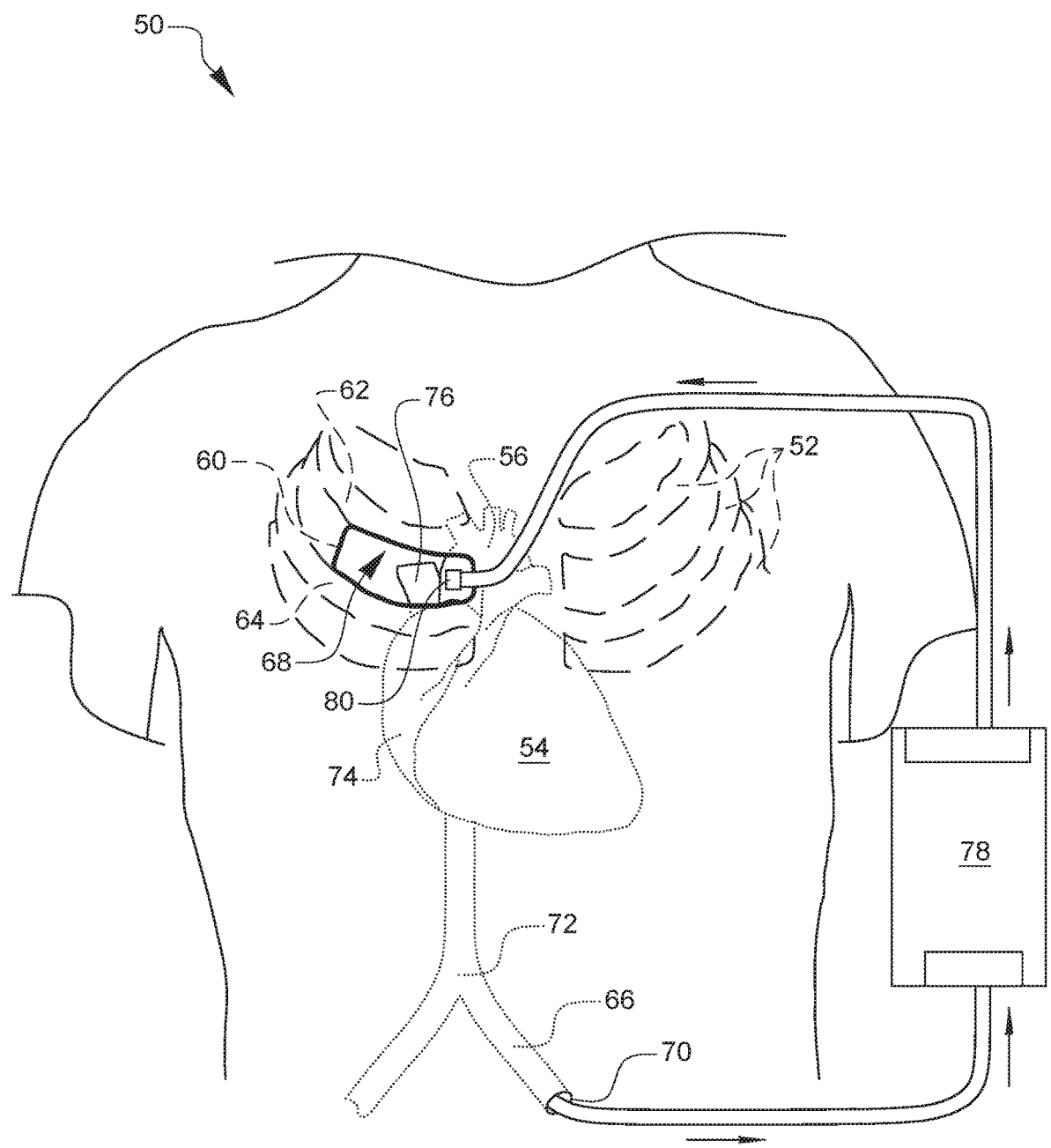
FIG. 2 schematically illustrates a cardiac surgical procedure performed through an intercostal space.
Figure 3A:
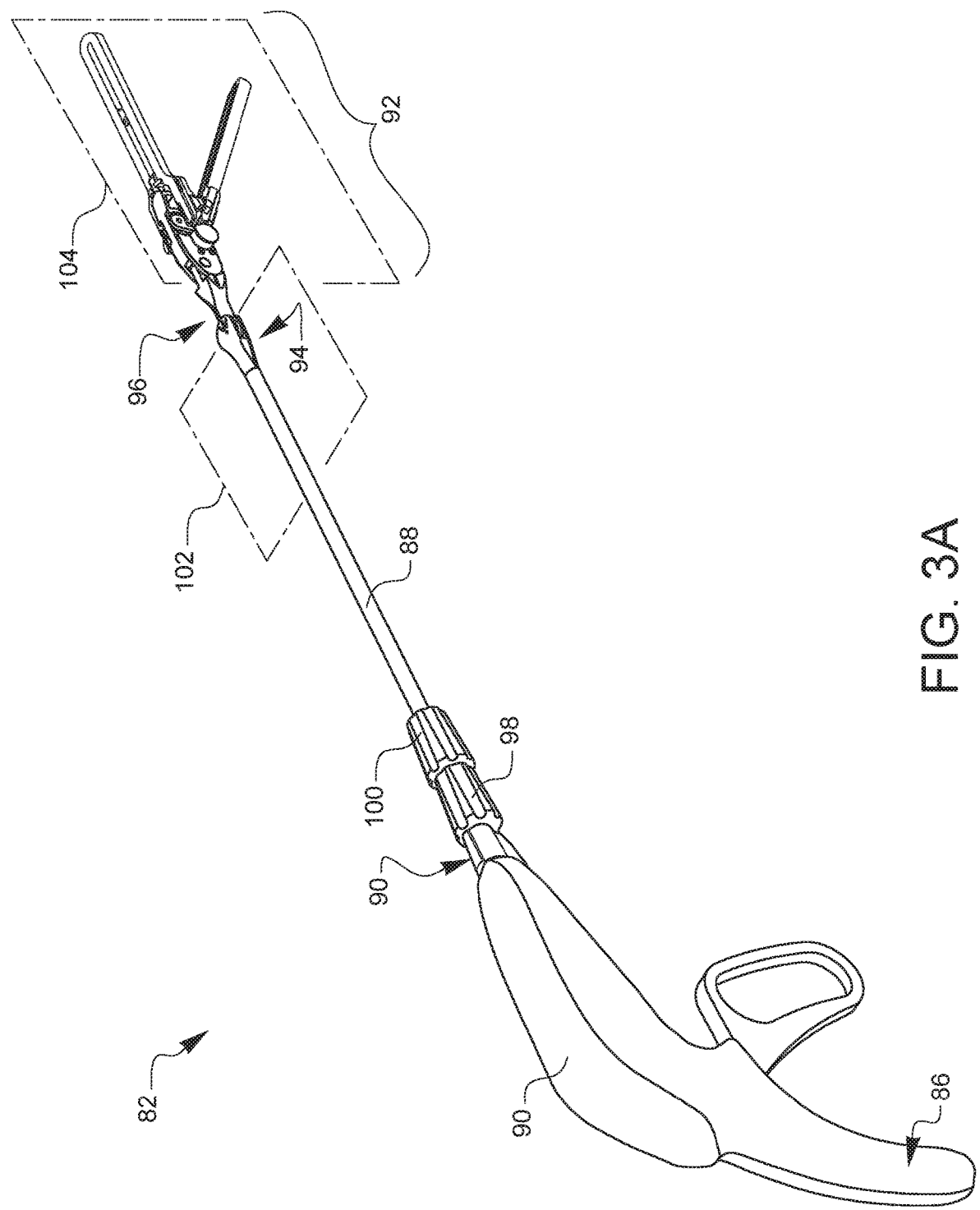
FIG. 3A is a perspective view of one embodiment of a minimally invasive surgical clamping device.

FIG. 3A is a perspective view of one embodiment of a minimally invasive surgical clamping device 82. The device 82 has a housing 84 which extends down to form a handle 86. The minimally invasive surgical clamping device 82 also has a shaft 88 which is coupled to the housing 84 by a rotational adapter which is not completely visible in this view. An indicator fin 90 of the rotational adapter can be seen in this view, however. The indicator fin 90 also defines a suture tube guide, also not visible in this view.

The surgical clamping device 82 has a clamping end 92 at the distal end 82D which is pivotably coupled to the shaft 88 by first and second articulation joints 94, 96. The first articulation joint 94 is operationally coupled to a first articulation knob 98 such that rotation of the first articulation knob 98 causes the first articulation joint 94 to articulate the clamping end 92 in a first plane 102. The second articulation joint 96 is operationally coupled to a second articulation knob 100 such that rotation of the second articulation knob 100 causes the second articulation joint to articulate the clamping end 92 in a second plane 104. In this example, the first plane 102 is substantially perpendicular to the second plane 104. In other embodiments having two articulation joints, the two articulation planes may not be substantially perpendicular. Other embodiments may have more or fewer, including none, articulation joints. The articulation joints in other embodiments may be capable of movement in more than one plane.

Figure 3B:
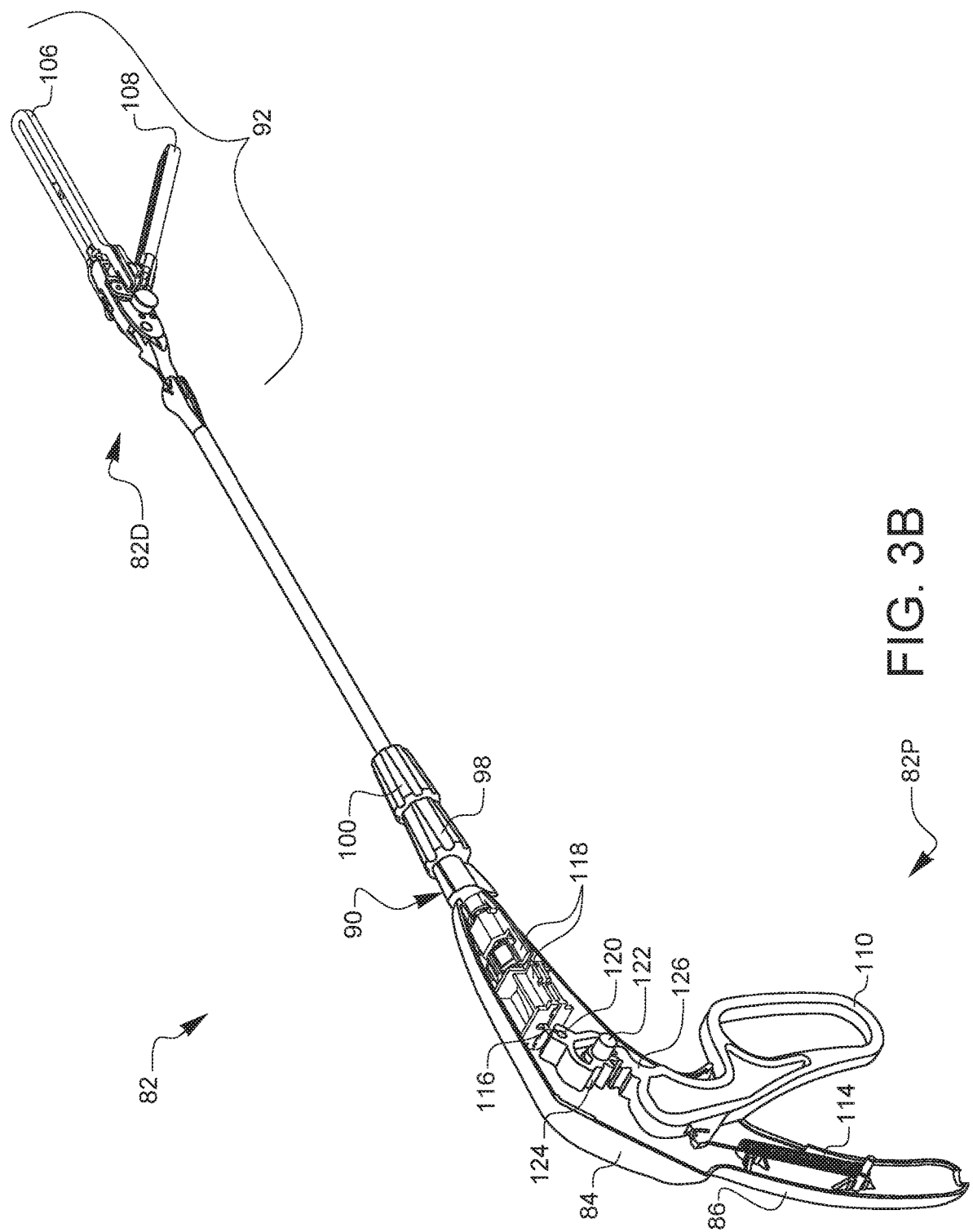
FIG. 3B is a partially exposed view of the minimally invasive surgical clamping device of FIG. 3A.

FIG. 3B is a partially exposed view of the minimally invasive surgical clamping device 82 of FIG. 3A. In particular, part of the housing 84 has been removed so that the components inside may be more clearly seen. The clamping end 92 of the minimally invasive surgical clamping device 82 includes a first clamping jaw 106 and a second clamping jaw 108. As will be explained in more detail later, the minimally invasive surgical clamping device 82 may be positioned such that the clamping end is advantageously positioned around a blood vessel, such as an aorta. The first clamping jaw 106 and the second clamping jaw 108 are configured to be movable around tissue or a blood vessel for clamping during a minimally invasive surgical procedure requiring an aortic cross clamp or similar clamping for the purpose of restricting blood flow through a vessel. The clamping jaws 106, 108 are coupled to an actuation lever 110 which is pivotable around pivot point 122. A biasing element, such as spring 114 is coupled between the actuation lever 110 and the inside of the handle 86 in order to keep the lever 110 biased away from the handle 86 as illustrated in the retracted or open position of FIG. 3B. In this retracted or open position, the clamping jaws 106, 108 remain open at the distal end of the minimally invasive surgical clamping device 82.

The clamping jaws 106, 108 are coupled to the lever 110 by a clamping control wire 116 (not fully visible in this view) which runs through the second and first articulation joints 98, 100, the shaft 88, and a rotation adapter 118. Embodiments of rotation adapters 118 are known to those skilled in the art. The proximal end of the clamping control wire 116, not fully visible in this view, has a ball which is coupled to the ball receiver 120. The ball receiver 120 is movable about a pivot point 122 and further defines a receiver gear 124. The receiver gear 124 is coupled to a lever gear 126 defined by the actuator lever 110. When the lever is actuated towards the handle 86, the lever gear 126 interacts with the receiver gear 124 in such a manner that the clamping control wire 116 is pulled towards the proximal end 82P of the device. Since the clamping control wire 116 is free to travel along its longitudinal axis when the actuation lever 110 is squeezed towards the handle 86, the clamping control wire 116, which is coupled to a mobile finger at the distal end 82D of the device, also pulls the mobile finger in a towards the proximal end 82P of the device, thus closing the clamping jaws 106, 108. Thus, the mobile finger and the fixed finger, which are not shown here but will be discussed later, constitute two fingers that are pivotable relative to one another. This is not shown in this view but will be discussed in regard to FIGS. 6A, 6B, 7A, and 7B.

Figure 4A:
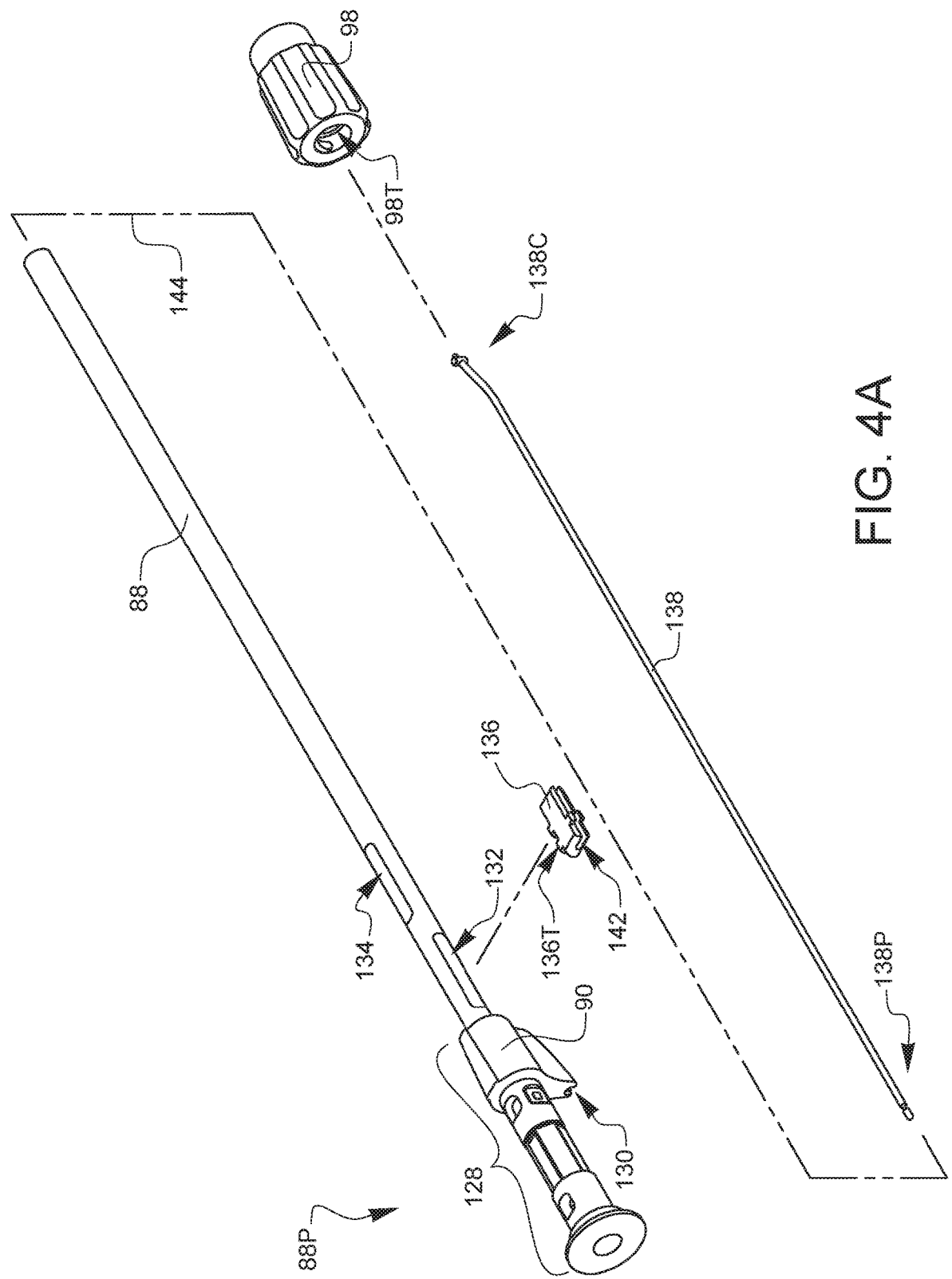
FIGS. 4A-4G are exploded views illustrating assembly of the minimally invasive surgical clamping device of FIG. 3A.

FIGS. 4A-4F are exploded views illustrating assembly of the minimally invasive surgical clamping device of FIGS. 3A and 3B. Referring to FIG. 4A, the shaft 88 is a hollow tube. As currently illustrated in FIG. 4A, the proximal end of the shaft 88P is attached to the inner rotation adapter 128. The shaft 88 and the rotation adapter 128 are not shown exploded, but the proximal end of the shaft 88P inside of the inner rotation adapter 128 has textured features around which the rotation adapter 118 is molded. The indicator fin 90 also defines a suture tube guide 130. The shaft 88 has first slot 132 and a second slot 134 formed near the proximal end of the shaft 88P. A first articulation rack 136 is placed in the first slot 132 and a proximal end 138P of a first articulation control wire 138 is placed into a distal opening 140 in the shaft 88. The proximal end 138P of the first articulation control wire 138 is configured to mate with a corresponding feature 142 on the first articulation rack. The first articulation rack 136 is shorter than the first slot 132, so it is able to be moved back and forth within the first slot 132 in a direction that is substantially parallel to the longitudinal axis 144 of the shaft 88. The first articulation knob 98 has threads 98T which are pitched to engage gear threads 136T on the first articulation rack 136. The first articulation knob 98 is passed over the shaft 88 and threaded onto the first articulation rack 136. A connector 138C on the distal end of the first articulation control wire 138 extends out of the shaft 88 and can be moved towards the distal opening 140 of the shaft 88 or away from the distal opening 140 of the shaft 88 to the extent that twisting the first articulation knob 98 is able to move the first articulation rack 136 within the first slot 132.

Figure 4B:
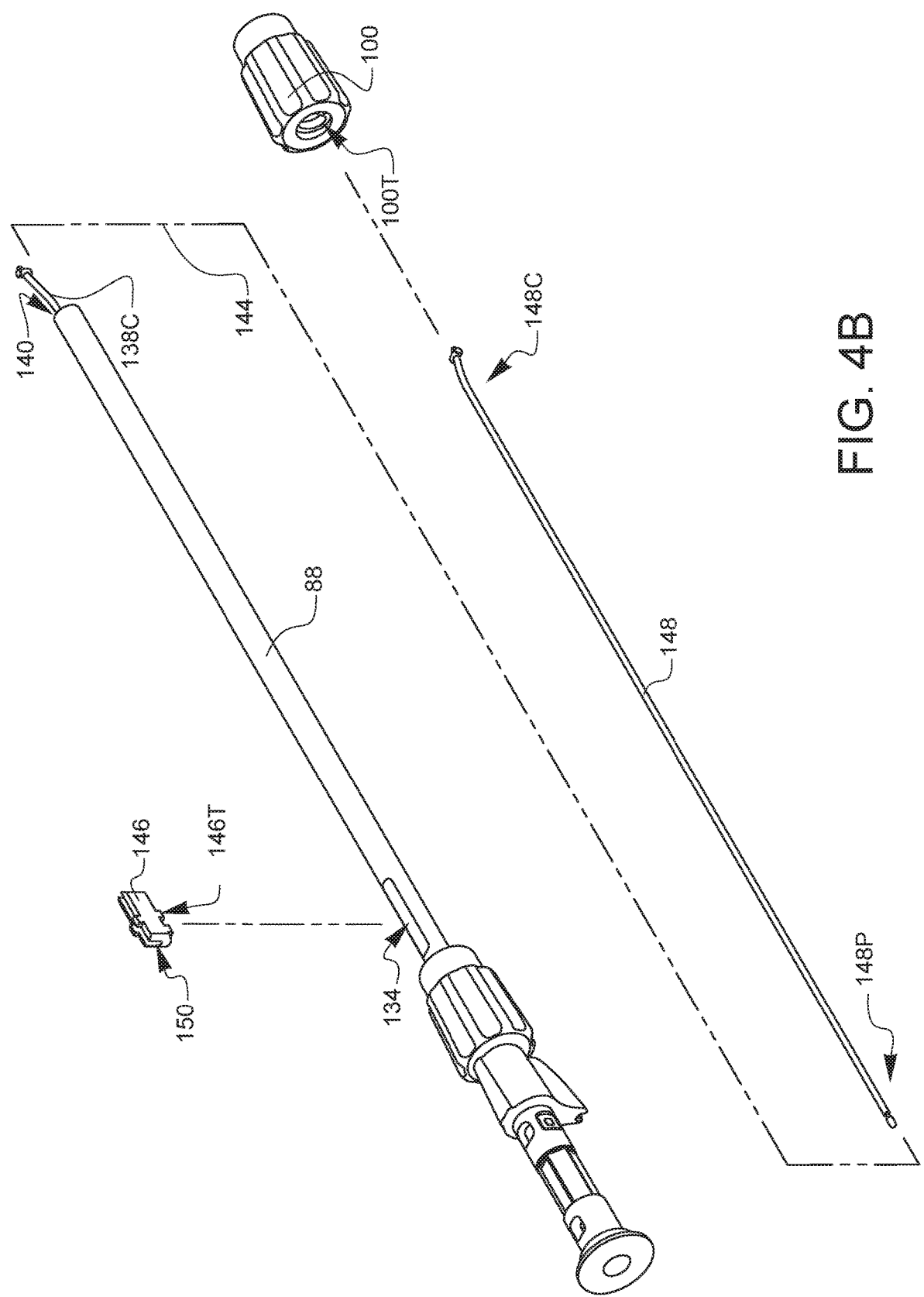

As shown in FIG. 4B, a second articulation rack 146 is placed in the second slot 134 and a proximal end 148P of a second articulation control wire 148 is placed into the distal opening 140 in the shaft 88. The proximal end 148P of the second articulation control wire 148 is configured to mate with a corresponding feature 150 on the second articulation rack 146. The second articulation rack 146 is shorter than the second slot 134, so it is able to be moved back and forth within the second slot 134 in a direction that is substantially parallel to the longitudinal axis 144 of the shaft 88. The second articulation knob 100 has threads 100T which are pitched to engage gear threads 146T on the second articulation rack 146. The second articulation knob 100 is passed over the shaft 88 and threaded onto the second articulation rack 146. A connector 148C on the distal end of the second articulation control wire 148 extends out of the shaft 88, farther than the first connector 138C, and can be moved towards the distal opening 140 of the shaft 88 or away from the distal opening 140 of the shaft 88 to the extent that twisting the second articulation knob 100 is able to move the second articulation rack 146 within the second slot 134.

Figure 4C:
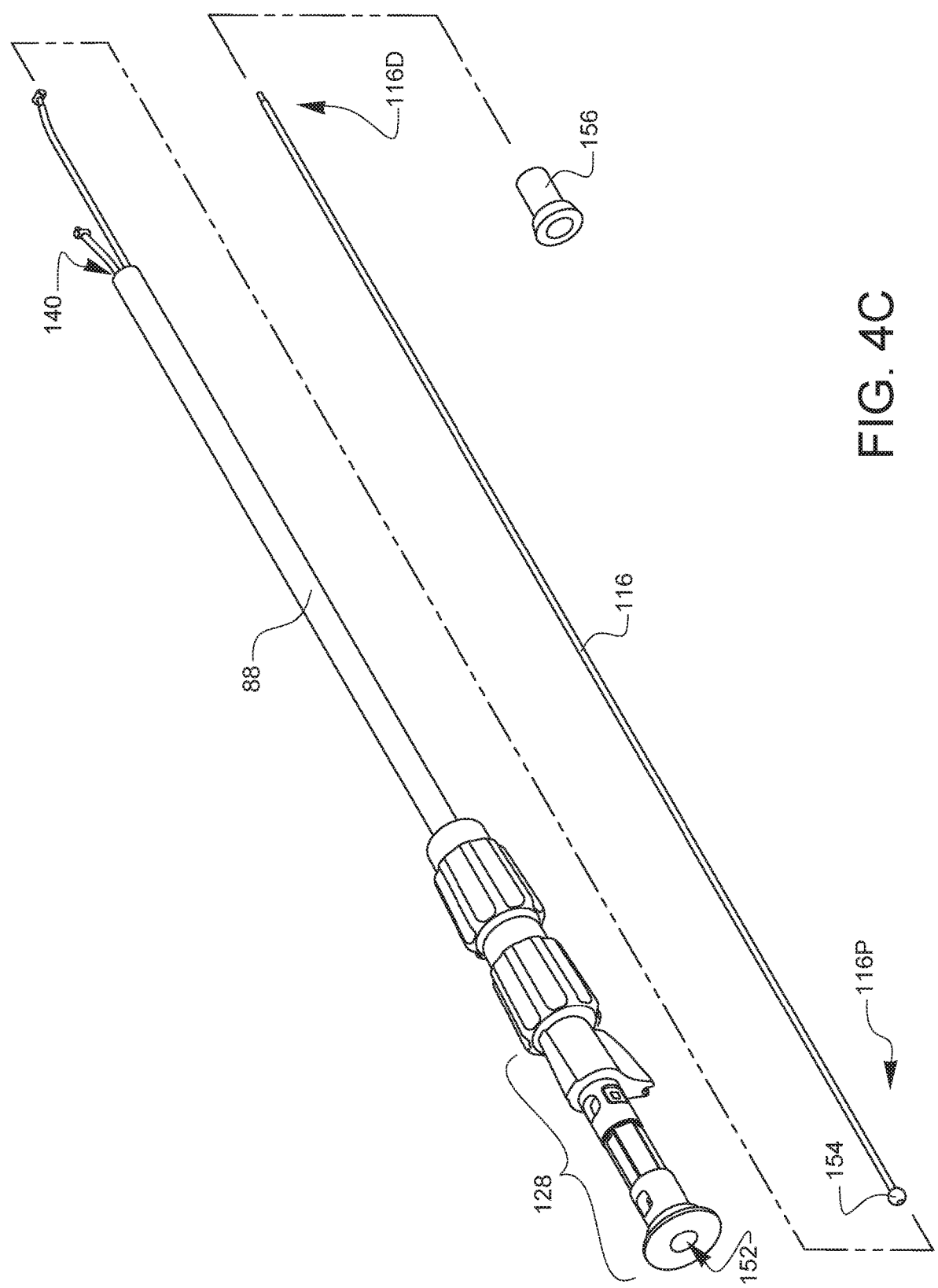

As shown in FIG. 4C, a proximal ball end 154 is attached to the proximal end 116P of the clamping control wire 116. The proximal end 116P of the needle control wire is inserted into the distal opening 140 of the shaft 88 and passed all the way through the shaft 88, through the inner rotational adapter 128, and out the actuator input 152 of the rotational adapter. A collar 156 is passed over the distal end 88D of the shaft 88 and fixed in place against the second articulation knob 100 to permanently hold the subassembly shown in FIGS. 4A-4C in place.

Figure 4D:
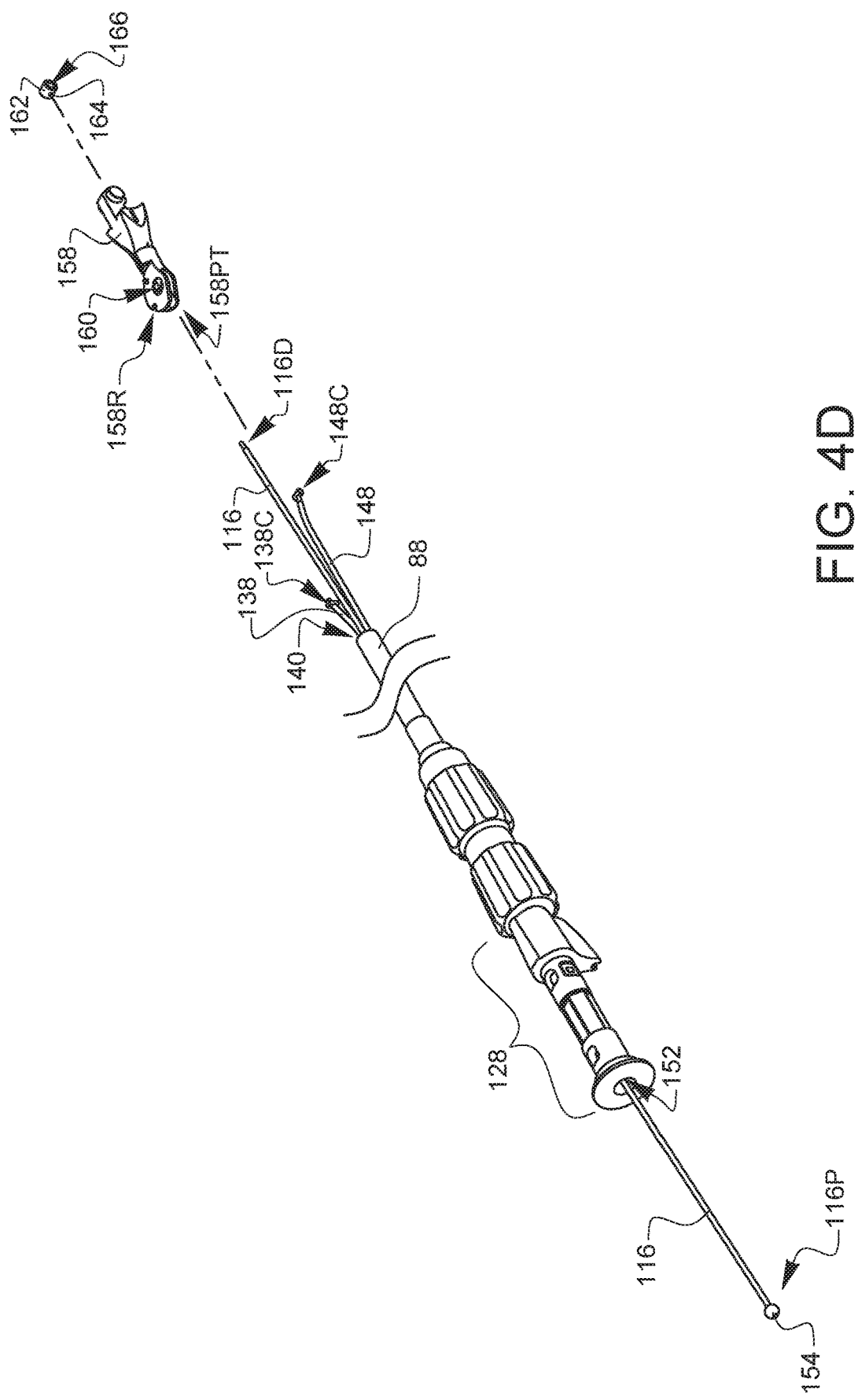

As illustrated in FIG. 4D, the proximal end 116P of the clamping control wire 116 is passed through the shaft 88 and protrudes from the actuator input 152 of the rotation adapter 128. The proximal ball end 154 is attached to the proximal end 116P of the clamping control wire 116. The proximal ball end 154 is coupled to the ball receiver 120 of actuation lever 110 as shown in FIG. 3B. The housing 84 and one or more rotation adapter receivers (not shown here) stabilize the inner rotation adapter 128. For simplicity, FIG. 4D does not show the housing 84, actuation lever 110, spring 114, or the rotation adapter receiver 124 so that the assembly of the distal end of the device may be seen more clearly. Recall that the first articulation control wire 138 and the connector 138C at its distal end protrude from the distal opening 140 of the shaft 88. Similarly, the second articulation control wire 148 and the connector 148C at its distal end protrude farther from the distal opening 140 of the shaft 88. Furthermore, the clamping control wire 116 protrudes even father from the distal opening 140 of the shaft 88. As illustrated in FIG. 4D, a first pivotable arm 158 has a first connector receiver 158R and a pass-through channel 158PT. The clamping control wire 116 and the second articulation control wire 148 are fed through the pass-through channel 158PT in the arm 158, and then the arm 158 is positioned so the first connector receiver 158R receives the connector 138C from the first articulation control wire 138. The first pivotable arm 158 also has an axle receiving opening 160, which will be further discussed in regard to FIG. 4E. A hollow cylindrical barrel 162 having an axle hole 166 along the axial length of the barrel 162 is attached to the clamping control wire 116 by inserting and fixing the distal end 116D of the clamping control wire into a hole 164 on the curved surface of the barrel 162.

Figure 4E:
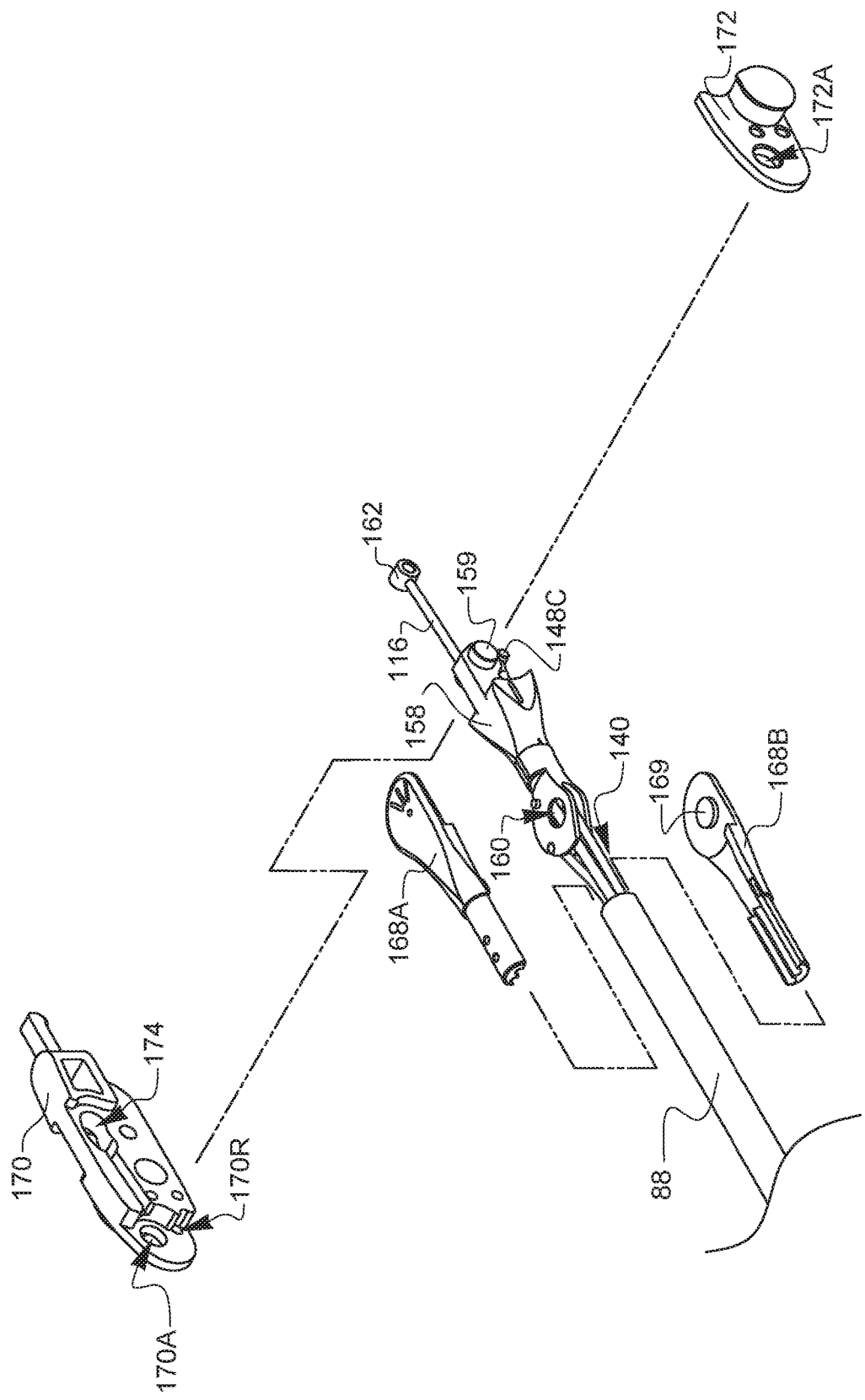

As illustrated in FIG. 4E, two fixed arm halves 168A, 168B are inserted into the distal end 140 of the shaft 88 while being brought together around the first pivotable arm 158. The fixed arm halves 168A, 168B each have an axle 169 (only one of which is visible in FIG. 4E). The axles 169 are aligned with the axle receiving opening 160 on the first pivotable arm 158. Together, the first pivotable arm 158 and the fixed arm halves 168A, 168B which support and provide an axle for the first pivotable arm 158 make up the first articulation joint 94 first discussed in FIG. 3A. Movement of the first articulation control wire 138 caused by rotation of the first articulation control knob 98 will cause the first pivotable arm 158 to pivot or articulate with respect to the fixed arm halves 168A, 168B. A fixed finger 170 having a barrel groove 174, an articulation recess 170R and an axle receiver 170A and a finger cover 172 having a finger cover axle receiver 172A and a corresponding articulation recess, not shown in this view, are placed over first pivotable arm 158 such that the barrel 162 is aligned with the barrel groove 174, the connector 148C at the distal end of the second articulation control wire 148 is constrained within the fixed finger articulation recess 170R and the corresponding recess on the finger cover 172, and that axle receiver 170A and axle receiver 172A align with an axle 159 on either side of the first pivotable arm 158. The barrel groove 174 is configured to limit the travel of the mobile finger in a prescribed space constrained by the geometry of the barrel 162 within the corresponding barrel groove 174. Together, the fixed finger 170 and the finger cover 172 make up the second articulation joint 96 first discussed in FIG. 3A. Movement of the second articulation control wire 148 caused by rotation of the second articulation control knob 100 will cause the combined fixed finger 170 and finger cover 172 to pivot or articulate with respect to the pivotable arm 158.

Figure 4F:
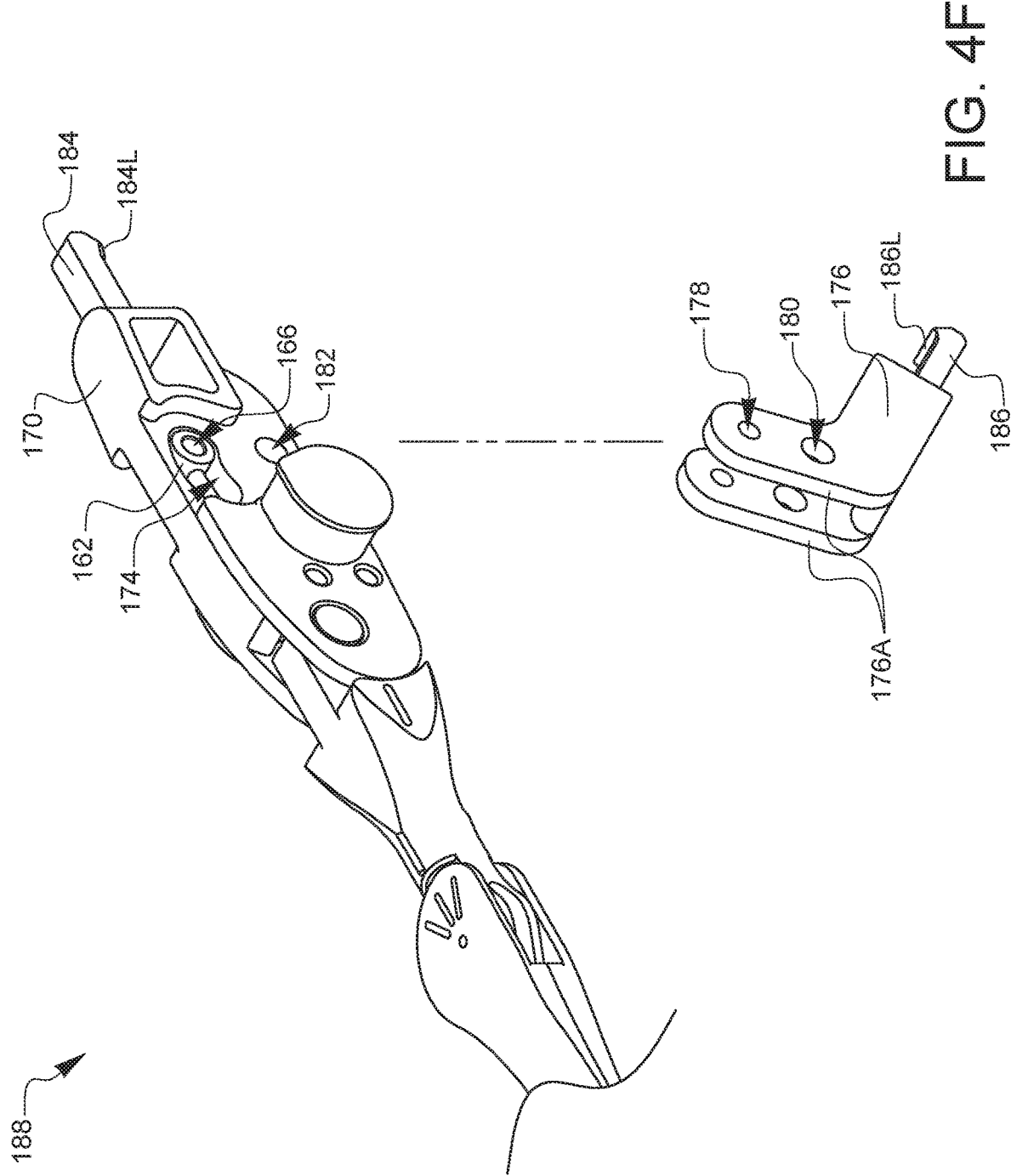

As illustrated in FIG. 4F, a mobile finger 176 defines two arms 176A, each arm 176A having a hole 178 and a pivot hole 180 configured to mount the mobile finger 176 onto the barrel 162 and onto hole 182, respectively. Each arm 176A is slidably engaged onto either side of the fixed finger 170 such that each pivot hole 180 align with hole 182 on the fixed finger 170, and each hole 178 aligns with the hole 166 in the barrel 162. The mobile finger 176 further defines a finger tab 186 which is terminated with a latch 186L. A similar latch 184L terminates a finger tab 184 on the fixed finger 170. This subassembly illustrated in FIG. 4F may also be referred to as an actuator 188 for the surgical clamping device 82 first shown in 3A.

Figure 4G:
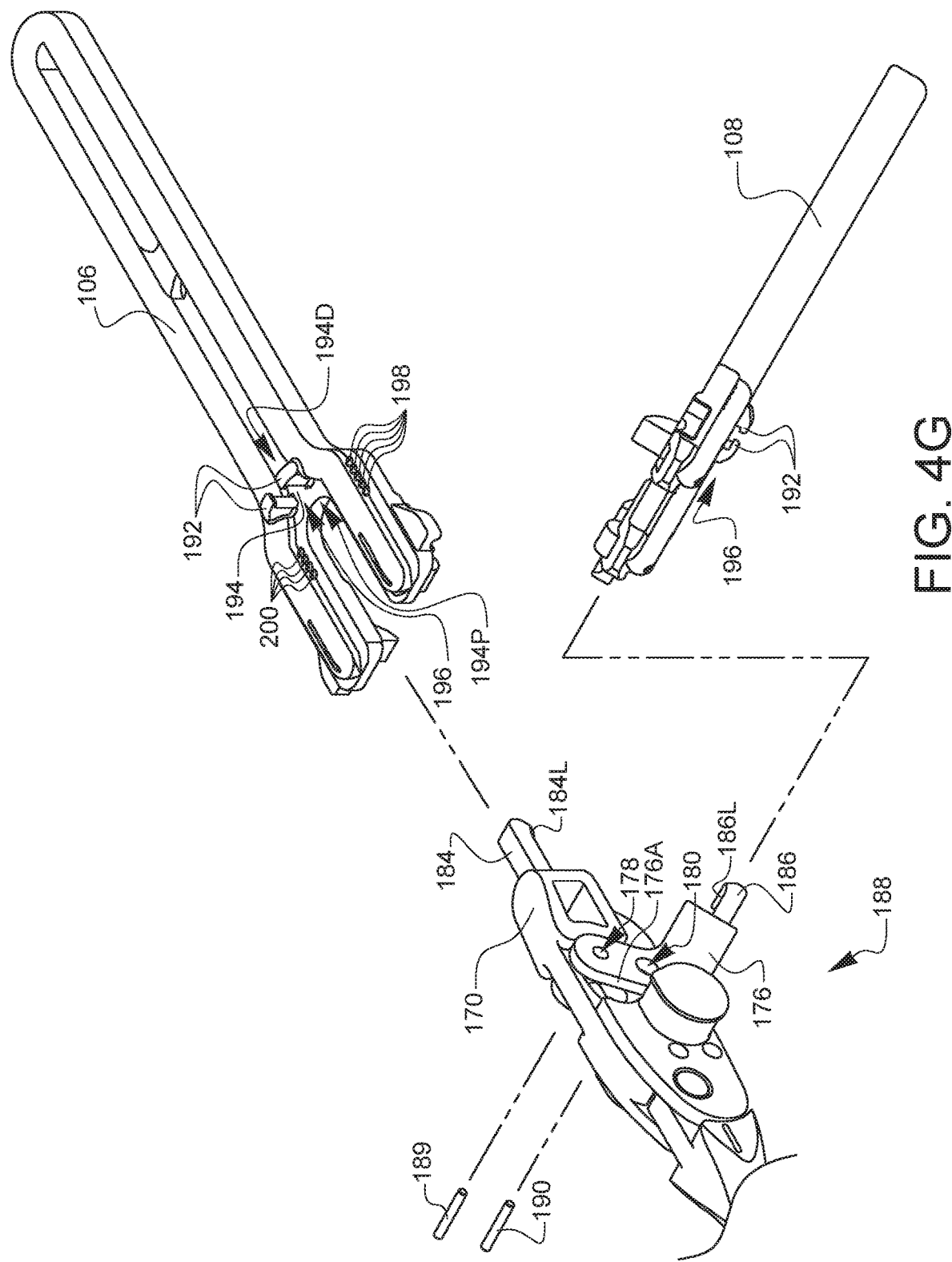

To complete the assembly as illustrated in FIG. 4G, an axle pin 189 is inserted through the hole 178 on the mobile finger arm 176A, through the barrel 162, and through the corresponding hole 178 on the opposing mobile finger arm 176A. A pivot pin 190 is then inserted through the pivot hole 180 on the mobile finger arm 176A, through the corresponding hole 182 on the fixed finger 170, finally through the corresponding pivot hole 180 on the opposite side of the mobile finger arm 176A. This configuration allows the mobile finger to pivot about the pivot pin 190 while traveling in an arc defined by travel of the barrel 162 in the groove 174 on the fixed finger, when actuated by the clamping control wire 116. This clamping actuation will be further described in regard to FIGS. 6A-7B.

The first clamp jaw 106 and the second clamp jaw 108 each further define a central structural point or central strut 194 on which there are two finger tab guides 192, which define an actuator interface 196. The clamp jaws 106, 108 also have several outer corset suture channels 198 and several inner corset suture channels 200, the purpose of which will be further described in regard to FIGS. 5A-5F. To install the first clamp jaw 106 onto the actuator 188, a fixed finger tab 184 on the fixed finger 170 is slidably engaged into the actuator interface 196 defined by the finger tab guides 192 on the strut 194 on first clamp jaw 106. The fixed finger tab 184 is pushed from the proximal end 194P towards the distal end 194D of the strut 194 until the latch 184L of the fixed finger tab 184 travels past the distal end 194D of the strut on the first clamp jaw 106 far enough to releasably hold the first clamp jaw 106 in place on the end of the fixed finger 170. Thus, both fingers 170, 176 can be slidably engaged with the actuator interfaces 196 on the first clamp jaw 106 and the second clamp jaw 108 simultaneously, or at approximately the same time.

The second clamp jaw 108 is installed in a similar manner as the first clamp jaw 106. The mobile finger tab 186 on the mobile finger 176 is slidably engaged into the actuator interface 196 defined by the finger tab guides 192 on the strut 194 second first clamp jaw 108. The mobile finger tab 186 is pushed from the proximal end 194P towards the distal end 194D of the strut 194 until the latch 186L of the fixed finger tab 186 travels past the distal end 194D of the strut on the second clamp jaw 108 far enough to releasably hold the first clamp jaw 108 in place on the end of the mobile finger 176. It should be noted that the finger tab guides 192 on both the first clamp jaw 106 and the second clamp jaw 108 are configured such that they accommodate the height of the fixed finger tab 184 and the latch 184L in the actuator interface 196 of either clamp jaw 106, 108. It should also be noted that while the clamp jaws 106, 108 in the embodiment illustrated in FIGS. 3A-3B and 4A-4G are identical, it is not required that they be so, and other clamp jaw configurations with different features allowing a slidable engagement of one or more clamp jaws with the actuator end 188 may be used. Likewise, attachment means other than the slidable engagement described may be used as well.

Figure 5A:
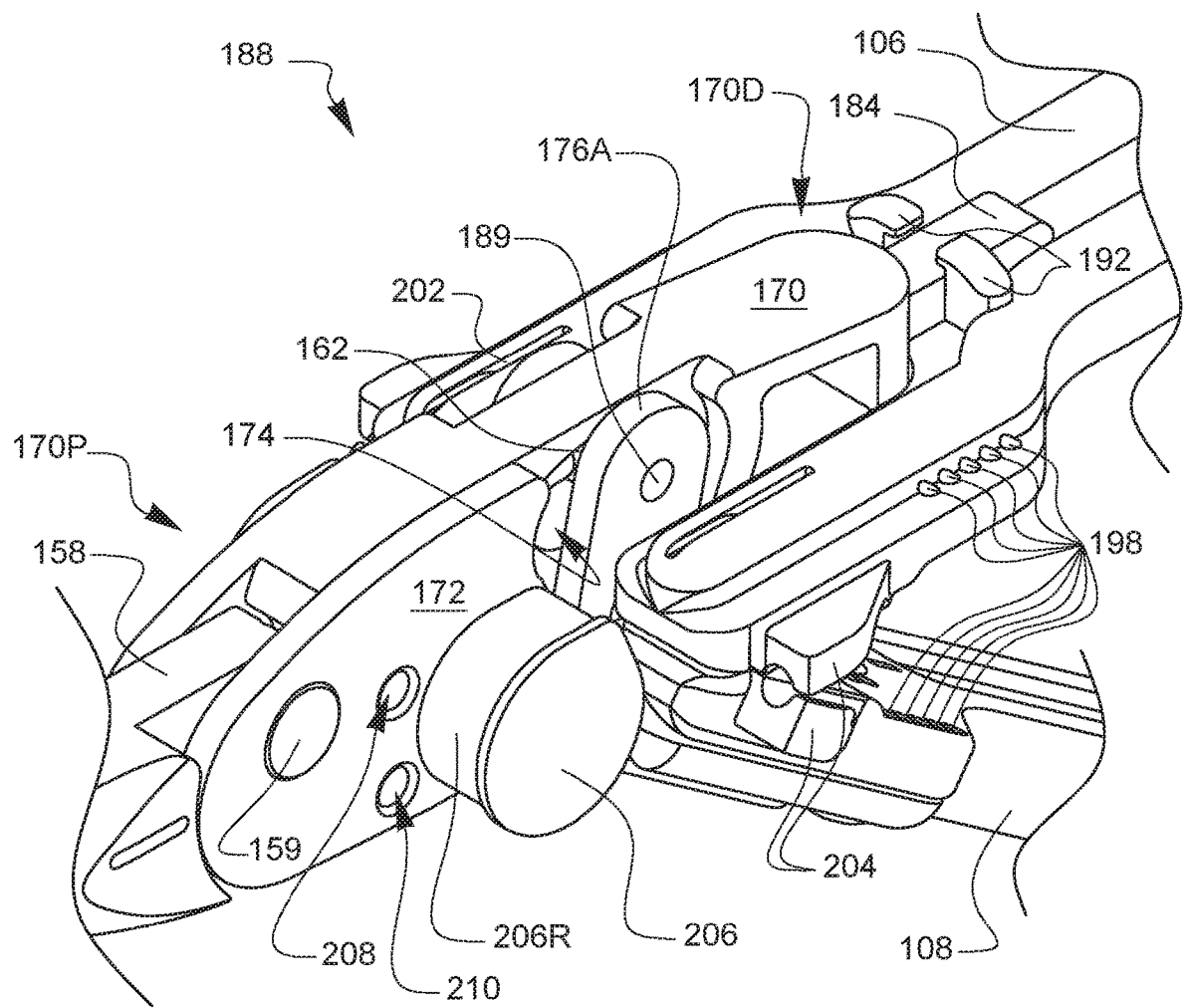
FIGS. 5A and 5B are top right perspective and top left perspective views, respectively, of an enlarged view of the intersection of an actuator end and a clamping end of the minimally invasive surgical clamping device of FIG. 3A.
Figure 5B:
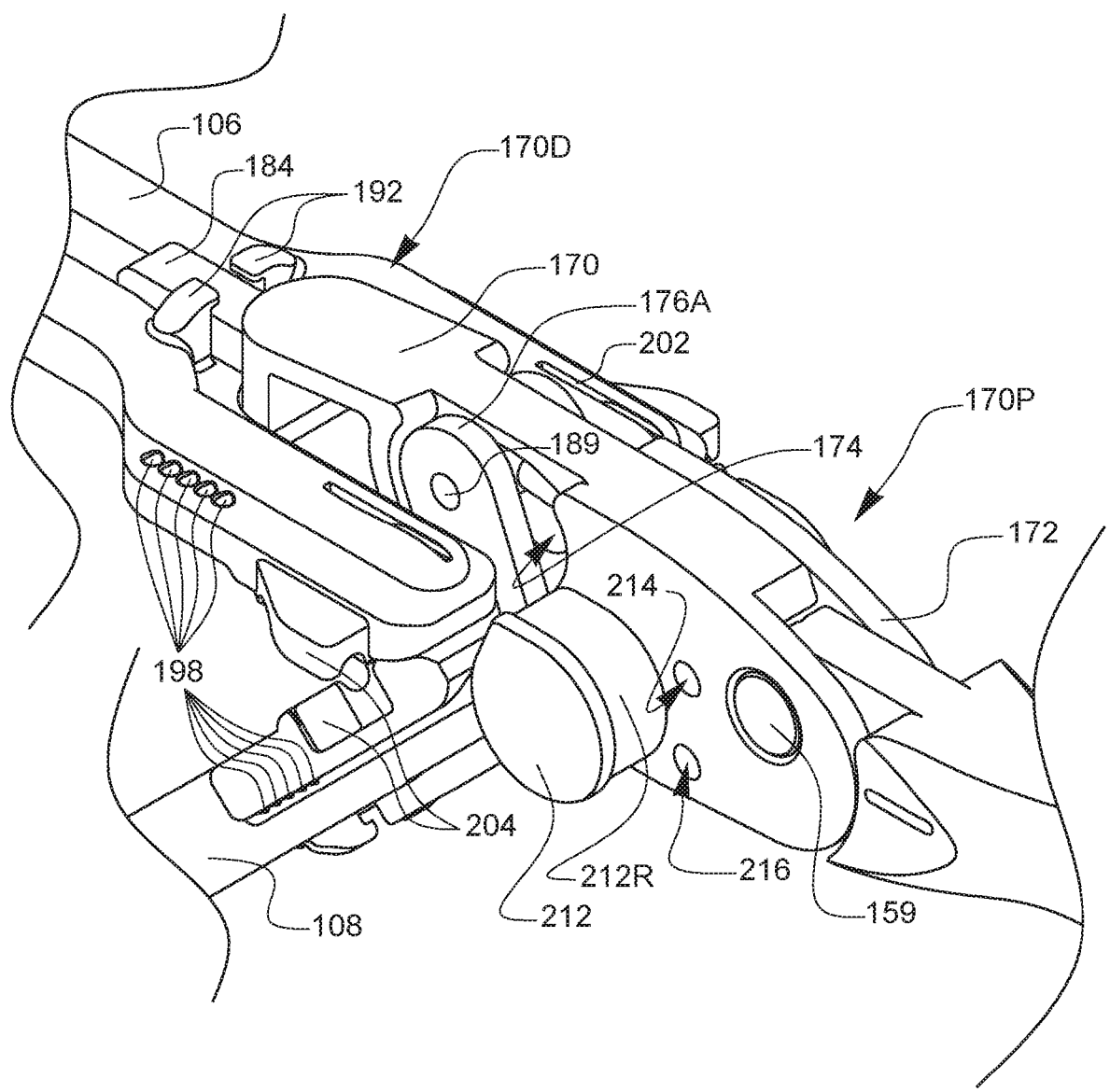

FIGS. 5A and 5B are top right perspective and top left perspective views, respectively, of an enlarged view of the intersection of an actuator end and a clamping end of the minimally invasive surgical clamping device of FIG. 3A. The enlarged view of FIG. 5A illustrates some of the additional features of this embodiment of the actuator 188 and the clamping end 92 of the minimally invasive surgical clamping device 82. As illustrated in FIG. 5A, the finger cover 172 further defines a windlass 206 and a windlass recess 206R, configured for receiving and winding a release suture around it to secure the clamp jaws 106, 108 in place after assembly or attachment of the clamp jaws 106, 108 to the actuator 188 as described in FIG. 4G. The finger cover 172 also has an upper suture channel 208 and a lower suture channel 210 configured to receive suture or suture tubes as required. The first clamp jaw 106 also has a release channel 202 on either side of the clamp jaw 106. The second clamp jaw 108 is identical in this embodiment and has identical release channels 202 and suture tube guides 204, although they are not as visible in this view. As shown in FIG. 5B, the fixed finger 170 also further defines a windlass 212 and a windlass recess 212R, configured for receiving and winding a release suture around it to secure the clamp jaws 106, 108 in place after assembly or attachment of the clamp jaws 106, 108 to the actuator 188 as described in FIG. 4G. The finger cover 172 also has an upper suture channel 208 and a lower suture channel 210 configured to receive suture or suture tubes as required.

Figure 5C:
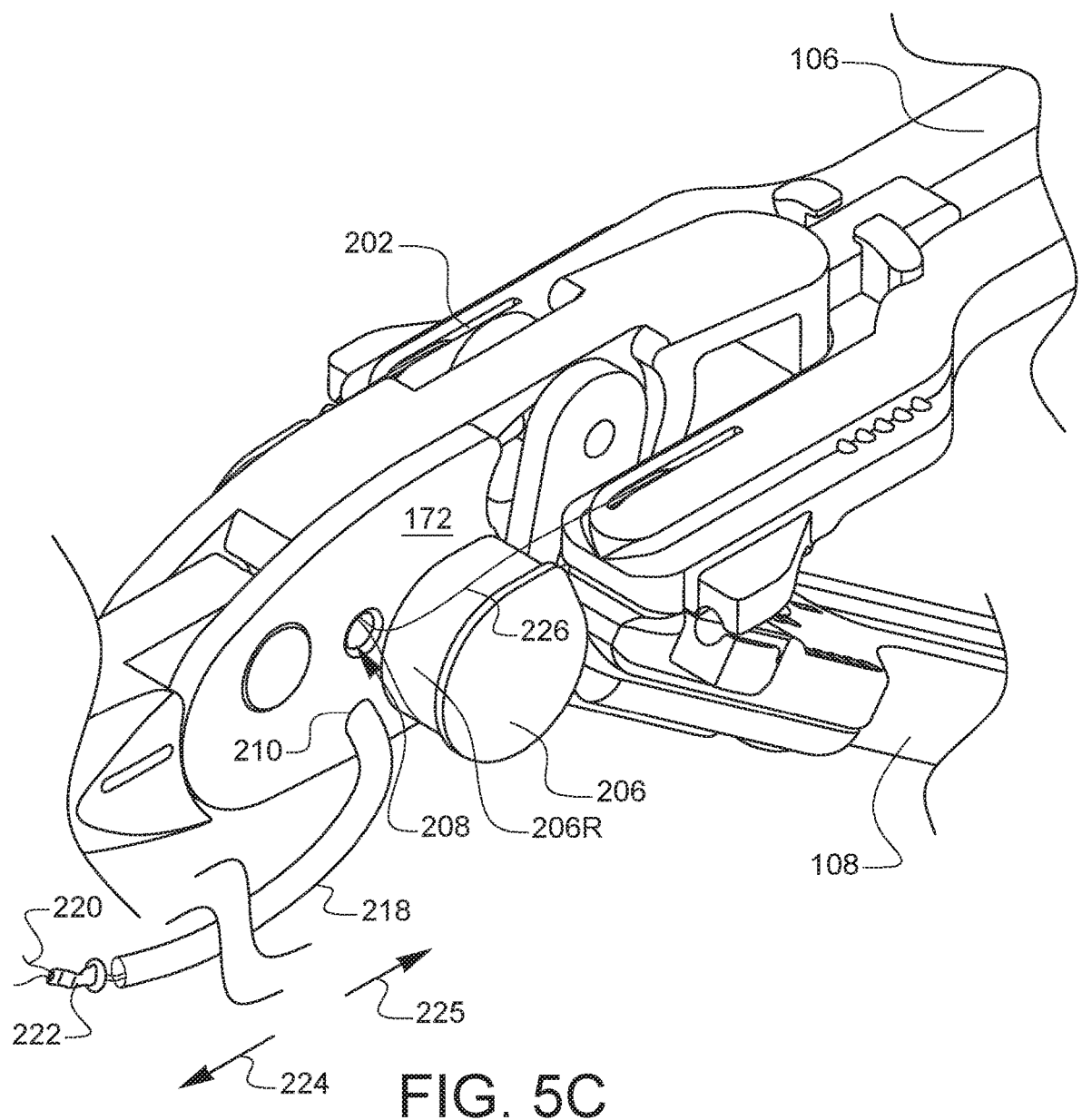
FIGS. 5C and 5D are top right perspective and top left perspective views, respectively, of an enlarged view of the intersection of an actuator end and a clamping end of the minimally invasive surgical clamping device of FIG. 3A, showing an assembly step of a release suture.
Figure 5D:
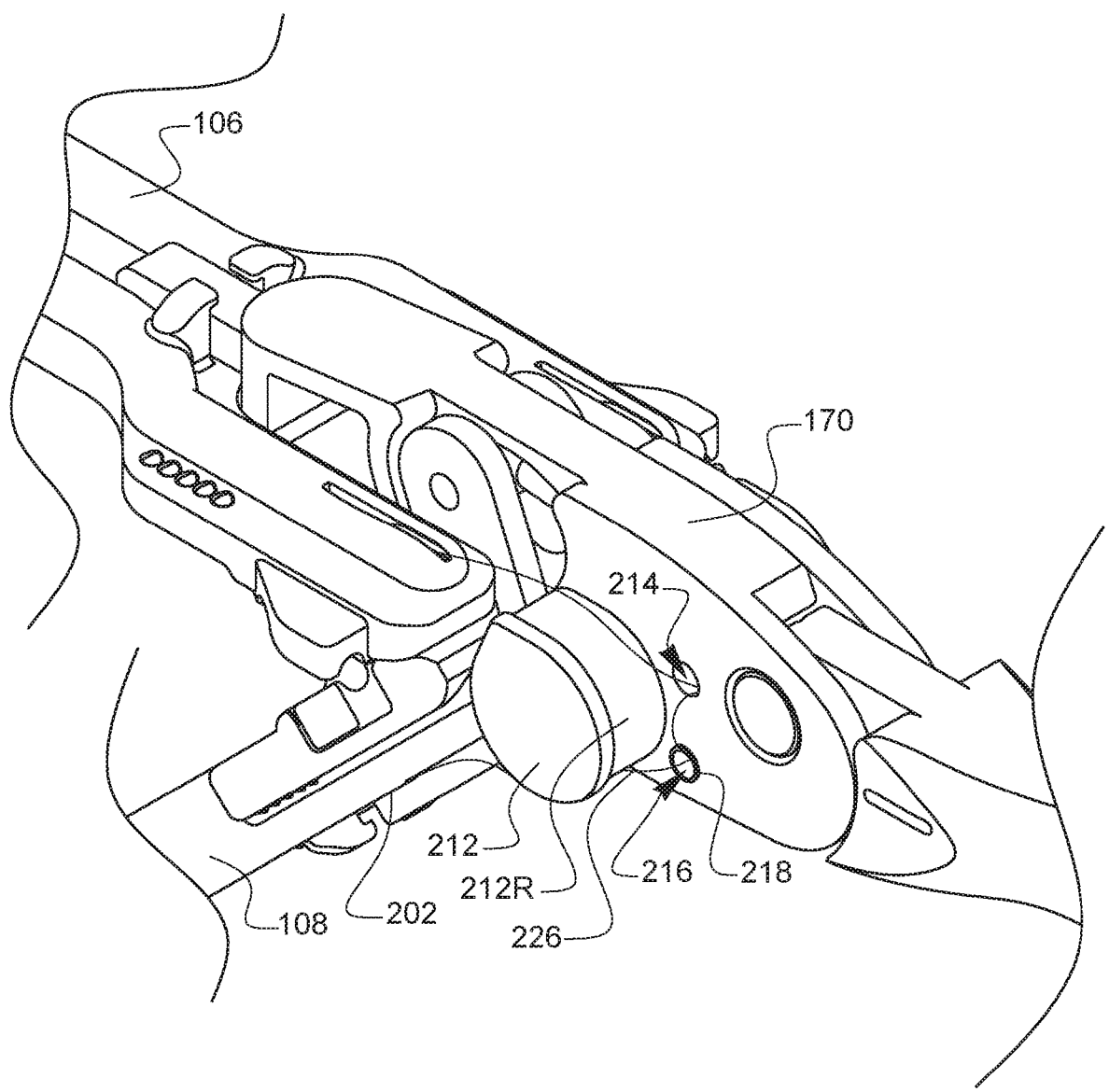

FIGS. 5C and 5D are top right perspective and top left perspective views, respectively, of an enlarged view of the intersection of an actuator end 188 and a clamping end 92 of the minimally invasive surgical clamping device 82 of FIG. 3A, showing an assembly step of a release suture 226. For illustrative purposes, the following description will alternate between opposite sides of the device in regard to FIGS. 5C and 5D. In the minimally invasive surgical clamping device 82 illustrated herein, there is also shown a release suture 226. The purpose of the release suture 226 is to provide a redundant security measure to ensure that the clamping end 92 will remain coupled to the actuator end 188 of the minimally invasive surgical clamping device 82 until such time that separation of the clamping end 92 from the actuator end 188 is desired by the operator. Assembly of the release suture 226 begins with a release suture 226 being threaded through a suture tube 218 and out of the end of the suture tube 218. The suture tube 218 is inserted into the lower suture channel 210 of the finger cover 172. The release suture 226 is then threaded through the lower suture channel 210 and out of the corresponding lower suture channel 216 in the fixed finger 170. The suture 226 is wound against the bottom side of the release windlass 212 on the fixed finger 170, into the release channel 202 of the second clamping jaw 108, and out of a corresponding release channel hole (not shown in this view) on the inward facing surface of the second clamp jaw 108. While the release suture is shown wrapped against the release windlass 212 in this view, it may also be wrapped around the release windlass 212 one or more times as desired before proceeding with the threading assembly through the release channel 202 on the second clamp jaw 108.

The release suture 226 is then threaded through a release channel 202 located on the inner side of the first clamp jaw 106 (not shown in this view) and out of a corresponding release channel 202 on the outer surface of the first clamp jaw 106. The shape of the release channels 202 on the clamp jaws 106, 108 are shown as a groove, or elongated channel in this embodiment. The purpose of this configuration is to direct the release suture 226 towards the windlass recess 206R, 212R on either side of the actuator 188, although the shape and configuration of the release channel 202 could be a variety of shapes or configurations known to those skilled in the art. The release suture 226 is then threaded over the top surface of the release windlass 212 in the recess 212R on the fixed finger 170, and into the upper suture channel 214 on the fixed finger 170. The release suture 226 is next threaded through the upper suture channel 214 and out of a corresponding upper suture channel 208 on the finger cover 172.

From here, the release suture 226 is wound against the top surface of the windlass recess 206R on the finger cover 172, into a release channel 202 on the outer surface of the first clamp jaw 106, out of a corresponding release channel on the inner surface of the first clamp jaw 106, into a release channel (not shown in this view) on the inner surface of the second clamp jaw 108, and out of a corresponding release channel on the outer surface of the second clamp jaw 108. The release suture 226 is then wound against the bottom side of the release windlass 206, and into and through the upper suture channel 208 on the finger cover 172. The suture 226 exits the upper suture channel 214 on the fixed finger 170 and into the suture tube 218, which is held in the lower suture channel 216. The two suture ends 220 of the release suture 226 are cinched tight and held in place remotely by pulling the suture ends 220 proximally towards 224 the user while pushing or holding the release suture tube 218 in a direction distally away 225 from the user. The release suture ends 220 are then secured with a mechanical fastener 222 such Ti-KNOT® and COR-KNOT® as sold by LSI Solutions, Inc. While a titanium mechanical fastener 222 is shown here, alternate means of securing the release suture ends such as a physical tied knot, clamps, or other suture locking device may also be used. While FIGS. 5C and 5D and the accompanying description demonstrate how to thread and secure the release suture 226, the minimally invasive surgical clamping device 82 may come pre-threaded and assembled in this configuration. Also, the threading may take alternate routes through the various channels in the components in the minimally invasive surgical clamping device 82 as further dictated by user preference or procedural necessity.

Figure 5E:
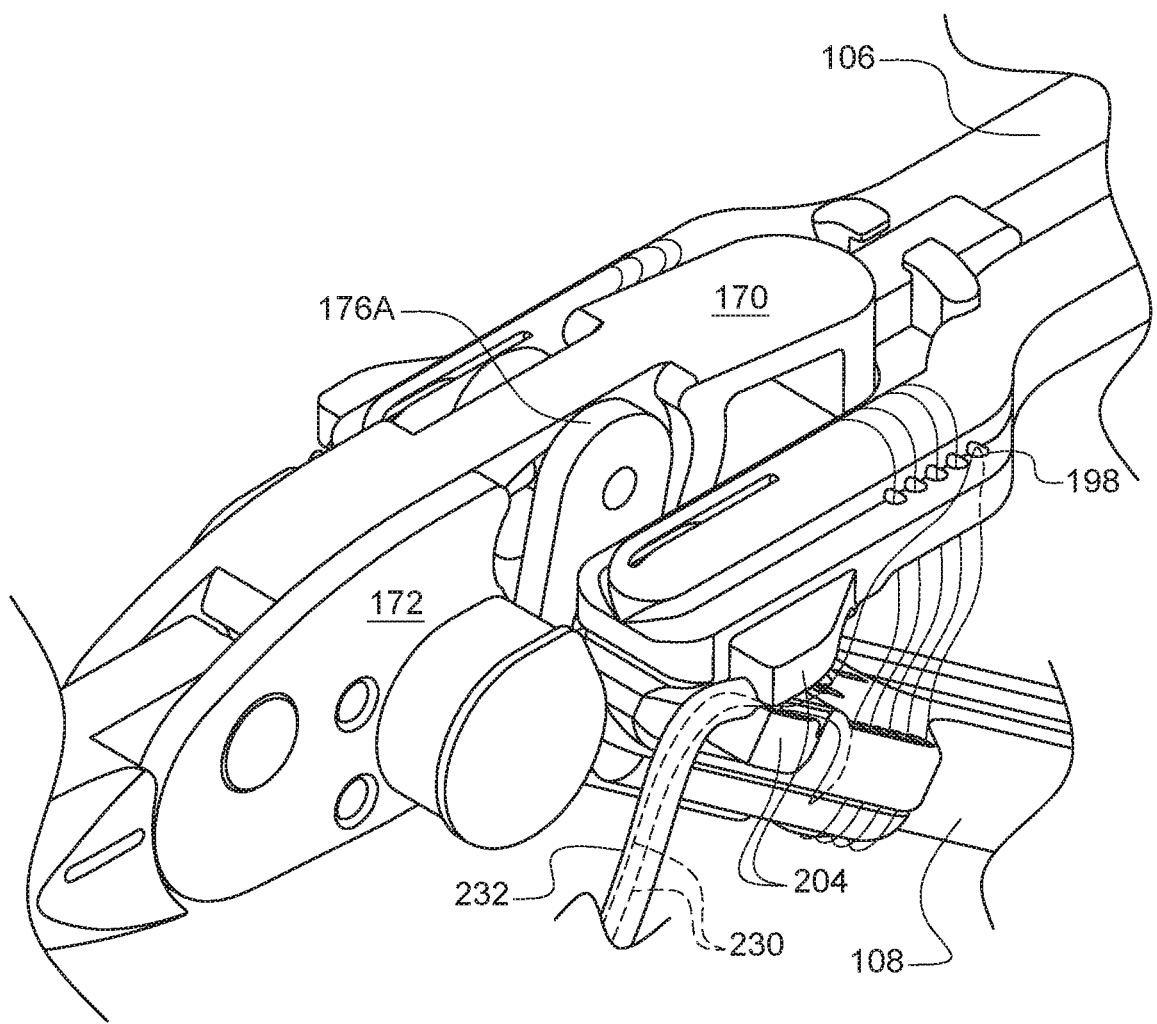
FIGS. 5E and 5F are top right perspective and top left perspective views, respectively, of an enlarged view of the intersection of an actuator end and a clamping end of the minimally invasive surgical clamping device of FIG. 3A, showing an assembly step of a corset suture.
Figure 5F:
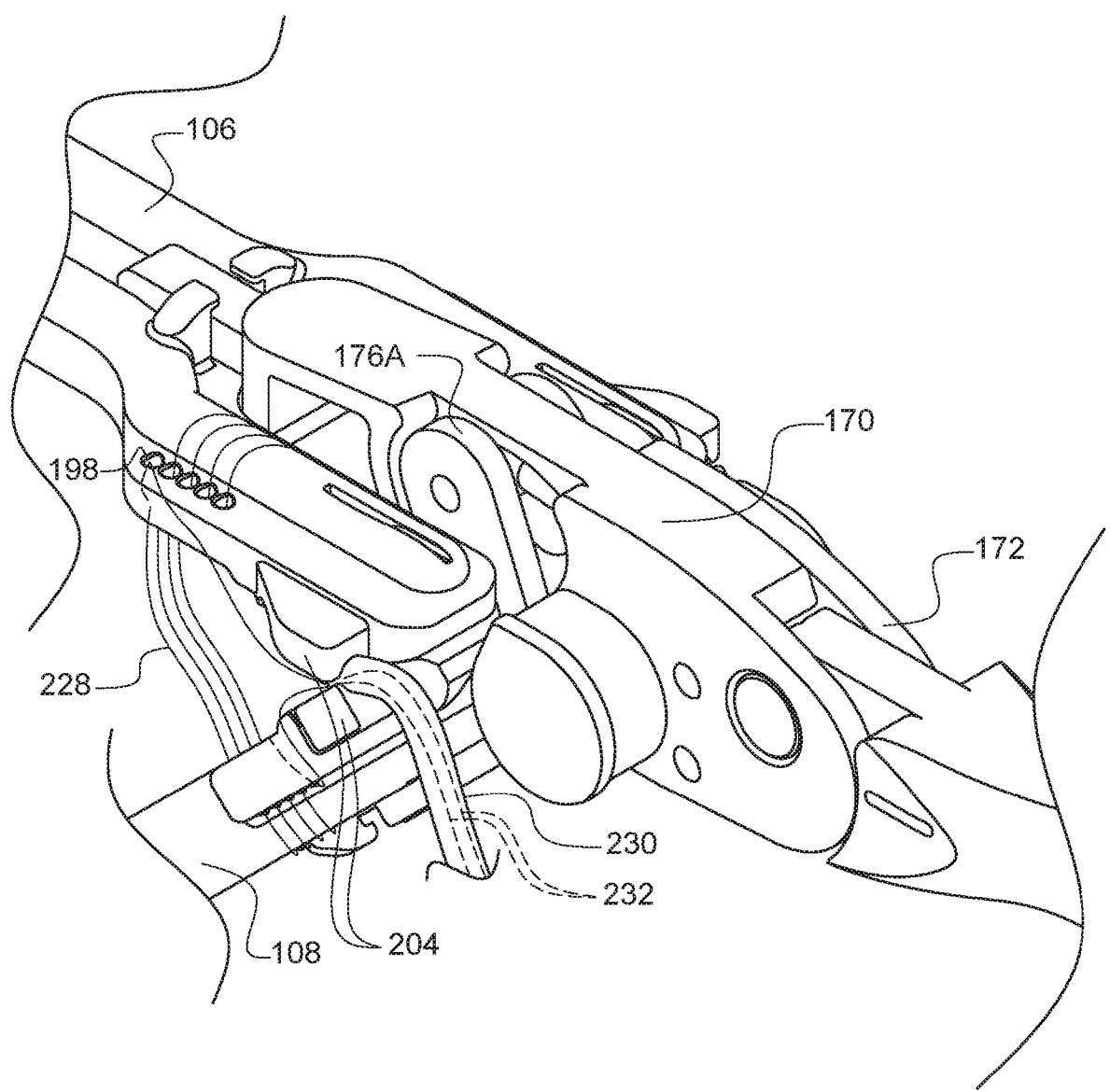

FIGS. 5E and 5F are top right perspective and top left perspective views, respectively, of an enlarged view of the intersection of an actuator end 188 and a clamping end 92 of the minimally invasive surgical clamping device 82 of FIG. 3A, showing an assembly step of a corset suture 228. For illustrative purposes, the following description will alternate between opposite sides of the device in regard to FIGS. 5E and 5F. For illustrative purposes, the following description will alternate between opposite sides of the device in regard to FIGS. 5E and 5F. The purpose of the corset sutures 228 is to maintain clamping pressure on a vessel once the surgical clamping device 82 has been actuated, and the clamping jaws 106, 108 placed in the desired location by the user. While corset sutures 228 can be assembled, threaded, and tightened on both sides of the embodiment of the clamping jaws 106, 108 described herein, the assembly and threading of only one side will be discussed in detail, as a similar threading procedure can be followed for the other side. Assembly of the corset suture 228 begins with threading a corset suture end 230 into the outer corset suture channel 198 on the first clamping jaw 106 and then down through to exit from the channel on the underside or inward facing surface of the first clamp jaw 106. Next, the end of the corset suture 228 is fed into a corresponding outer corset suture channel 198 on the inward facing surface of the second clamp jaw 108 and through to exit from the underside of the second clamp jaw 108. The corset suture 228 is then threaded around the underside of the second clamp jaw 108 and into an inner corset suture channel on the underside of the second clamp jaw (not shown here) to subsequently exit from the inner corset suture channel on the inward facing surface of second clamp jaw 108. The corset suture 228 is then threaded into a corresponding inner corset suture channel 200 located on the inward facing surface or underside of the first clamp jaw 106, exits from the inner corset suture channel 200 at the top side or outward facing surface of first clamp jaw 106, then around the top side or outward facing surface of the first clamp jaw 106, and into an outer corset suture channel 198 adjacent to the initial outer corset suture channel 198 where the threading began. These previous steps are repeated to thread the corset suture 228 through all available outer corset suture channels 198 and inner corset suture channels 200. Once this is completed, the corset suture 228 is threaded back through a corset suture tube 232 on either side of the clamp jaws 106, 108. Both ends of the corset suture 228 are now in a corset suture tube 232 and the corset suture tube 232 can be held between the mating corset suture tube guides 204 on both the first clamp jaw 106 and on the second clamp jaw 108 to facilitate suture management, as the corset sutures 228 are kept loose until they are tightened during a surgical procedure. It should be noted that fewer corset suture channels 198, 200 may be used, and other configurations or arrangements of threading may be used as desired by the user.

Figures 7A, 7B:
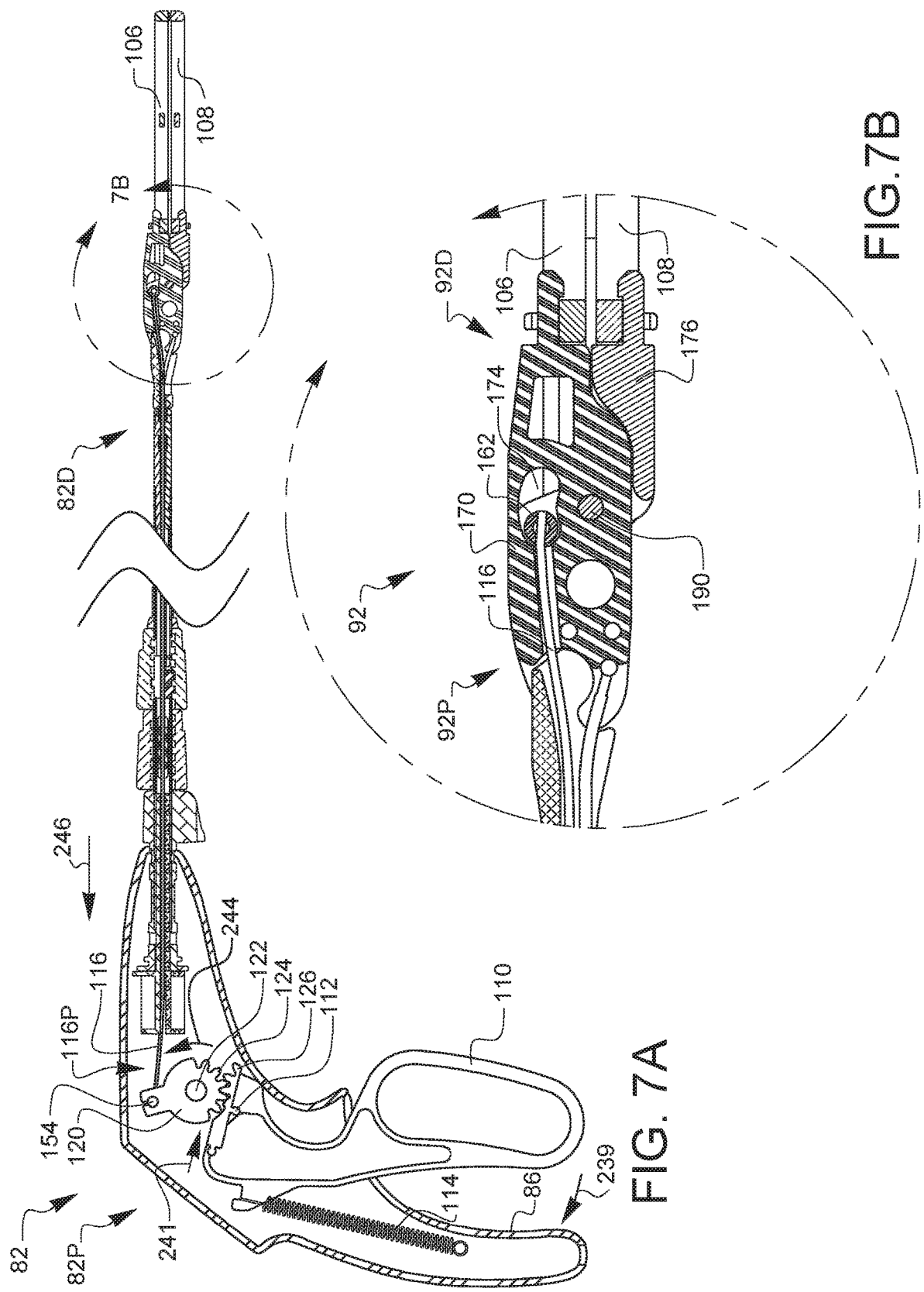

FIGS. 6A, and 7A are partial cross-sectional side views illustrating a suturing sequence using the minimally invasive surgical clamping device 82 of FIG. 3A. Each of FIGS. 6A, and 7A has a corresponding enlarged view, FIGS. 6B, and 7B, respectively. The enlarged views show the clamping end 92 in more detail. For convenience, only FIGS. 6A, and 7A will be discussed, but it should be understood that the enlarged views of FIGS. 6B, and 7B may also be consulted for more detail. Also, since FIGS. 6A, and 7A are from a side view, not all of the components described previously may be seen in these views. For convenience, therefore, only the visible components will be discussed, however, it is understood that there may be corresponding components in addition to the visible components.

In FIG. 6A, while the clamping end 92 is in the open position, the actuation lever 110 is in the unsqueezed position, the lever gear is positioned towards 237 the proximal end 82P of the minimally invasive surgical clamping device 82 and the first clamping jaw 106 and the second clamping jaw 108 remain open or apart. The ball end 154 in the ball receiver 120 is oriented in a direction 236 allowing the clamping control wire 116 to remain untensioned and in a direction towards 234 the distal end 82D of the surgical clamping device 82. At the clamping end 92, the barrel 162 is also positioned towards the distal portion 92D of the clamping end 92 within the groove 174 in the fixed finger 170. This untensioned state of the wire 116 and the position of the barrel 162 allow the mobile finger 176 to remain open about the pivot pin 190 and therefore the attached second clamp jaw 108 is open or apart from the first clamp jaw 106.

As shown in FIG. 7A, the lever 110 is squeezed towards 239 the handle 86. This moves the lever gear 126 in a direction 241, which also moves the ball receiver 120 and the ball end 154 in a direction 244 which tensions the clamping control wire 116 and pulls the wire 116 in a direction towards 246 the proximal end 82P of the surgical clamping device 82. This causes the distal end of the clamping control wire 116 to move the barrel 162 within the groove 174 of the fixed finger 170 towards the proximal end 92P of the clamping end 92, pivoting the mobile finger 176 about pivot pin 190, moving the mobile finger in a direction 248, and therefore closing the inward facing surface of the second clamp jaw 108 towards the inward facing surface of the first clamp jaw 106.

Figure 8C:
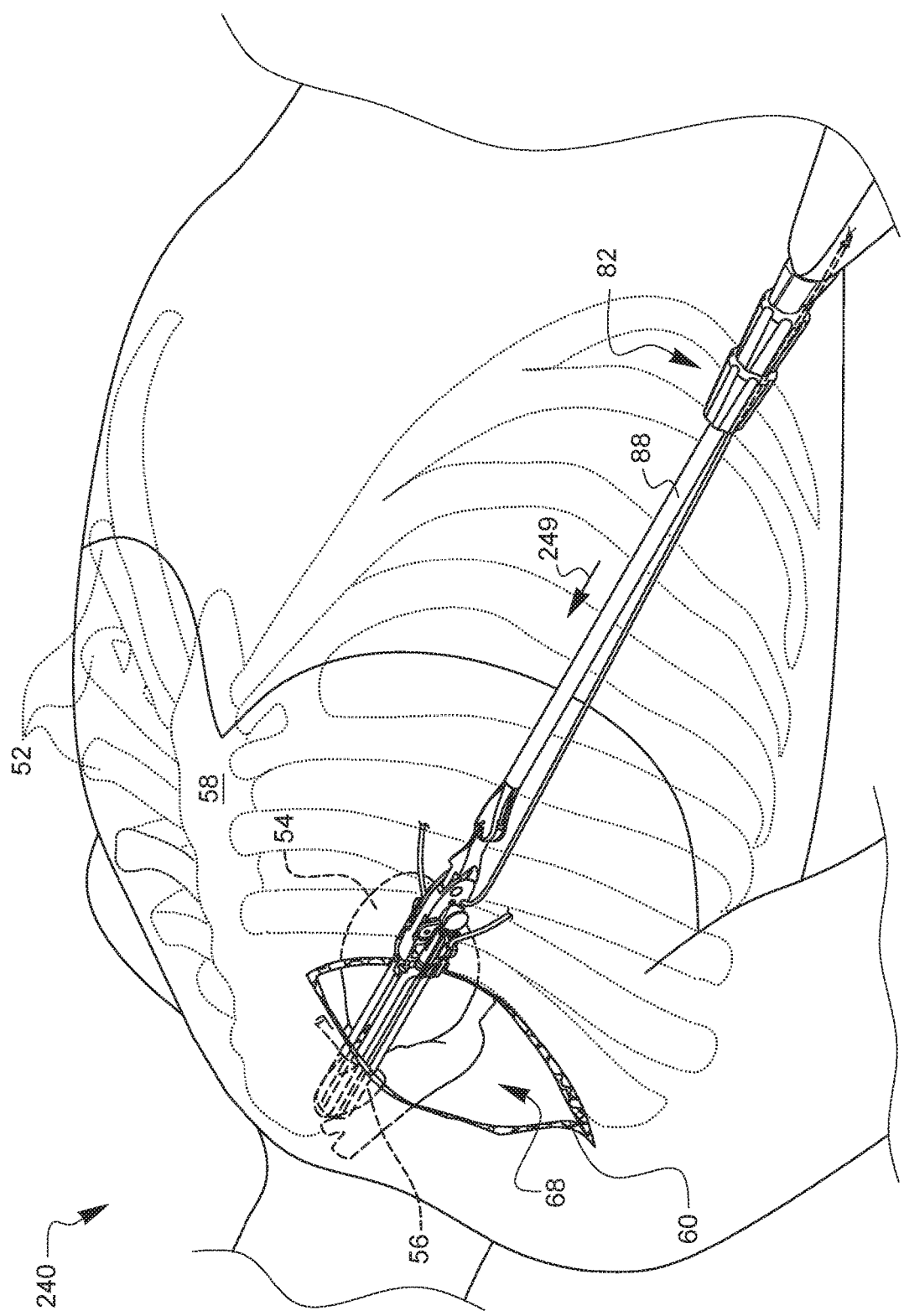
FIG. 8C is a perspective view of the minimally invasive surgical clamping device of FIG. 3A being inserted into an incision on the patient of FIG. 8A.

FIG. 8A is a perspective view of a chest area of a patient undergoing a surgical procedure. A patient 240 is shown in a prepared position for a minimally invasive surgical procedure. The location of the ribcage 52, sternum 58, second rib 62, and third rib 64 are shown. The location for a minimally invasive incision 60 in the intercostal region between the second rib 62 and the third rib 64 are also shown. FIG. 8B is a perspective view of the patient 240 of FIG. 8A and the minimally invasive surgical clamping device of FIG. 3A in the closed position. In FIG. 8B, the patient 240 of FIG. 8A is now shown with a minimally invasive opening 68 in preparation for the introduction of the surgical clamping device 82 of FIG. 3A into the minimally invasive opening 68. The relative location of the ribcage 52, heart 54, and aorta 56 are schematically illustrated. FIG. 8C is a perspective view of the distal end of the minimally invasive surgical clamping device of FIG. 3A being inserted into an incision on the patient of FIG. 8A. The surgical clamping device 82 is being inserted into the opening 68 in a direction 249 towards the aorta 56.

Figure 9A:
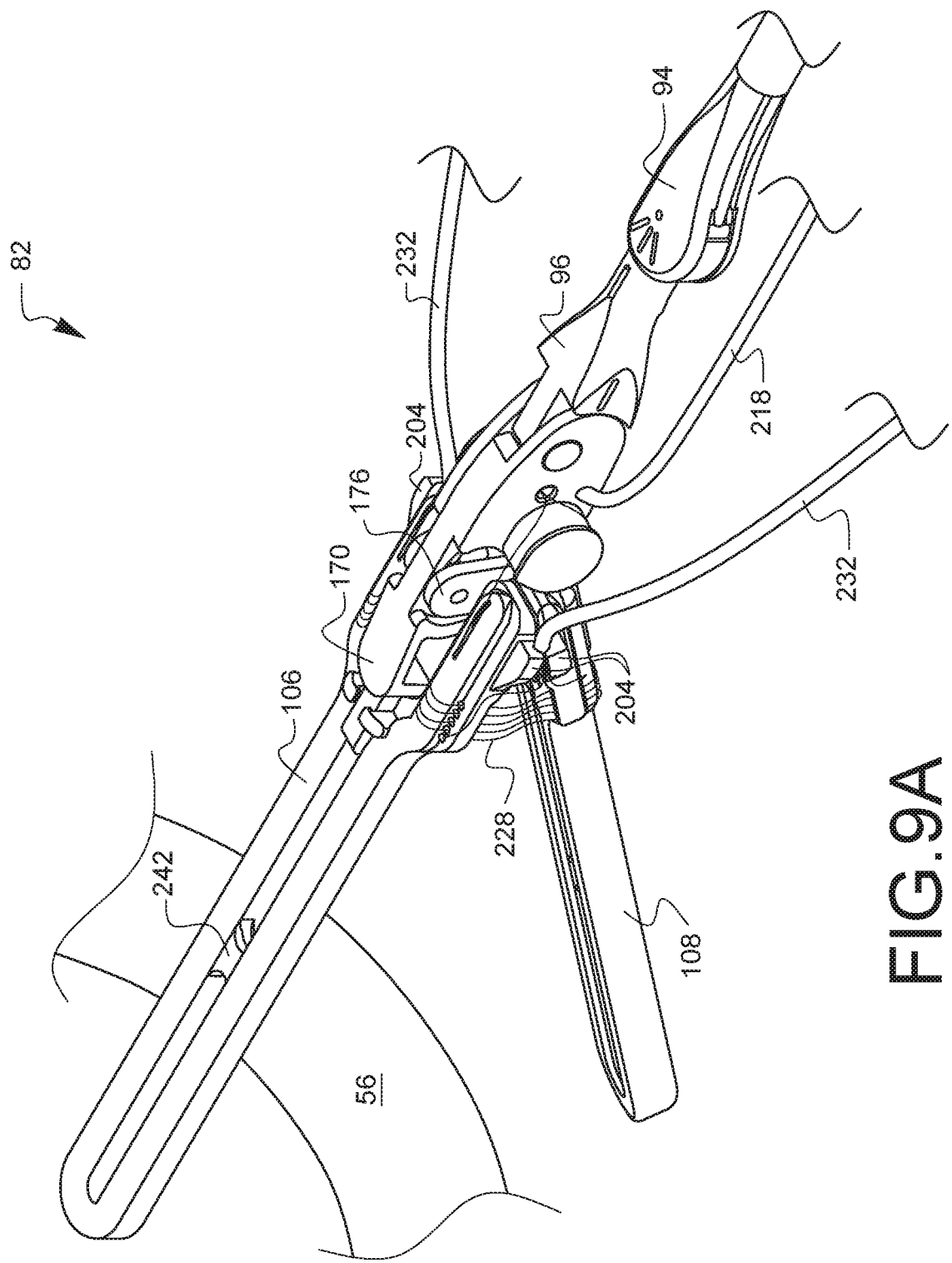
FIG. 9A is a perspective view of the surgical clamping device of FIG. 3A from inside a body cavity in an unclamped or open position.

FIG. 9A is a perspective view of the surgical clamping device of FIG. 3A from inside a body cavity in an unclamped or open position. The clamping end 92 of minimally invasive surgical clamping device 82 can be positioned via movement of the first articulation joint 94 and second articulation joint 96 as previously described. The positional indicator 242 located on the first clamp jaw 106 is used as a visual confirmation that the clamping jaws 106, 108 are in the desired position relative to the location of the aorta 56. While the clamping jaws 106, 108 are being placed around the aorta 56, the corset sutures 228 remain threaded, but loosely held so as to allow for pivotable movement of the second clamp jaw 108 attached to the mobile finger 176 relative to the first clamp jaw 106 attached to the fixed finger 170. At this stage, the corset sutures 228 are also retained within the corset suture tubes 232, and the corset suture tubes 232 are held in place and seated in the suture tubes guides 204 on either side of both clamp jaws 106, 108.

FIG. 9B is a perspective view of the surgical clamping device of FIG. 3A from inside a body cavity in a clamped or closed position. FIG. 9B illustrates the next step in the surgical procedure where the second clamp jaw 108 has moved in a direction 252 to close the clamp jaws around the aorta 56, thereby restricting blood flow and providing an aortic cross-clamp. The mechanism of movement of the surgical clamping device 82 has previously been described in regard to FIGS. 6A-6B and FIGS. 7A-7B. At this stage, the corset sutures 228 are still loose, and retained within the corset suture tubes 232. The corset suture tubes 232 are held in place and seated in the suture tubes guides 204 on either side of both clamp jaws 106, 108.

Figure 9C:
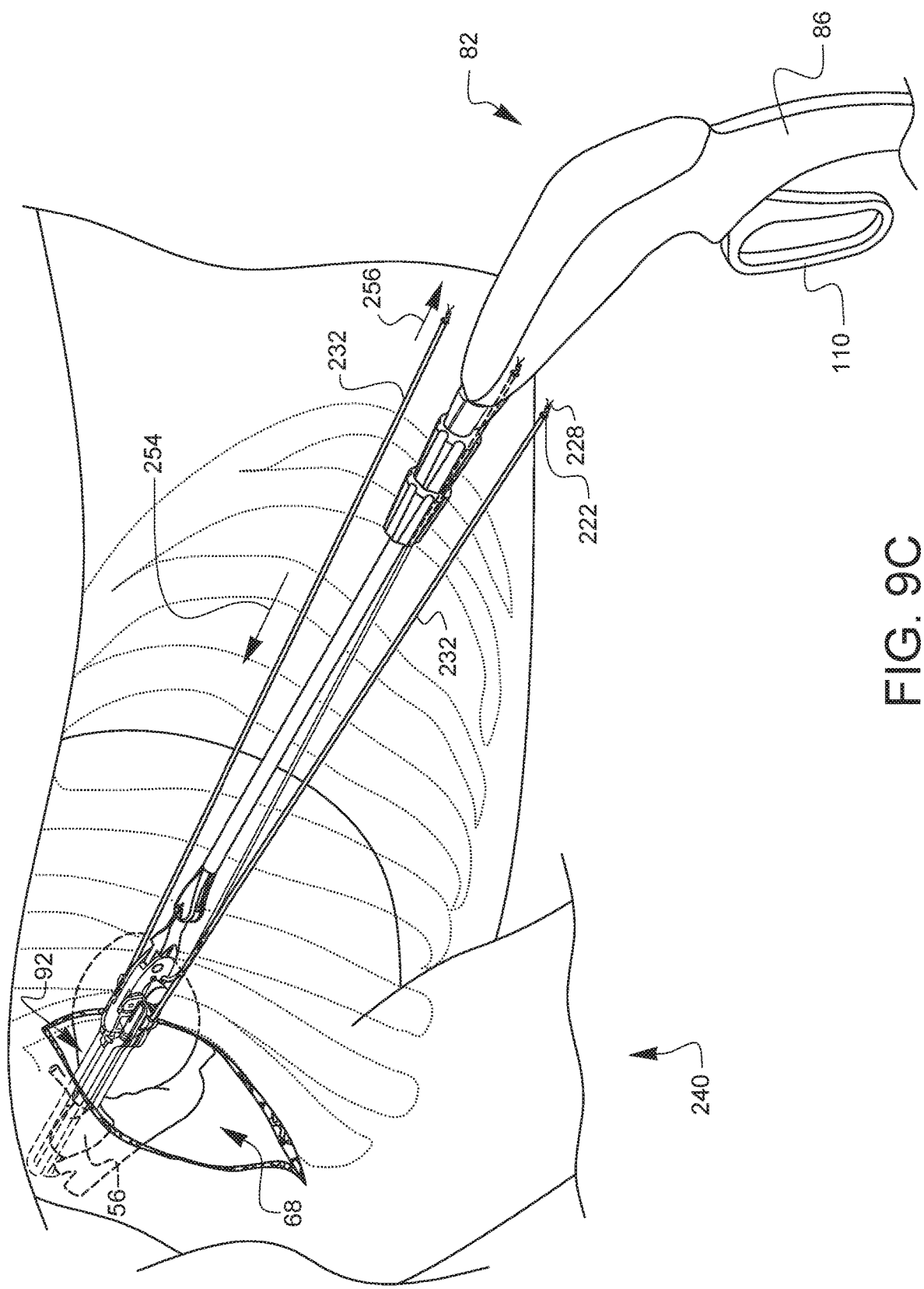
FIG. 9C is a perspective view of the surgical clamping device of FIG. 3A from outside a body cavity illustrating the tightening of two pair of corset sutures.

FIG. 9C is a perspective view of the surgical clamping device of FIG. 3A from outside a body cavity illustrating the tightening of two pair of corset sutures. Again, the patient 240 is shown with a minimally invasive opening 68 with the actuator lever 110 of the surgical clamping device 82 squeezed towards the handle 86, which continues to hold the clamping end 92 of the securely on the aorta 56. In order to maintain the clamping pressure provided to the clamping jaws 106, 108, the corset suture 228 threaded on either side of the clamp jaw 106, 108 is pulled in direction 256 while the corset suture tube 232 pushed in direction 254, which tightens the corset suture 228. The end of each corset suture 228 can then be clamped with a mechanical fastener 222 in order to maintain clamping pressure sufficient enough to provide effective aortic cross clamping during the surgical procedure. While a mechanical fastener 222 is shown in this view, other means known to those skilled in the art, such as forceps or suture locking devices may also be used.

Figure 9D:
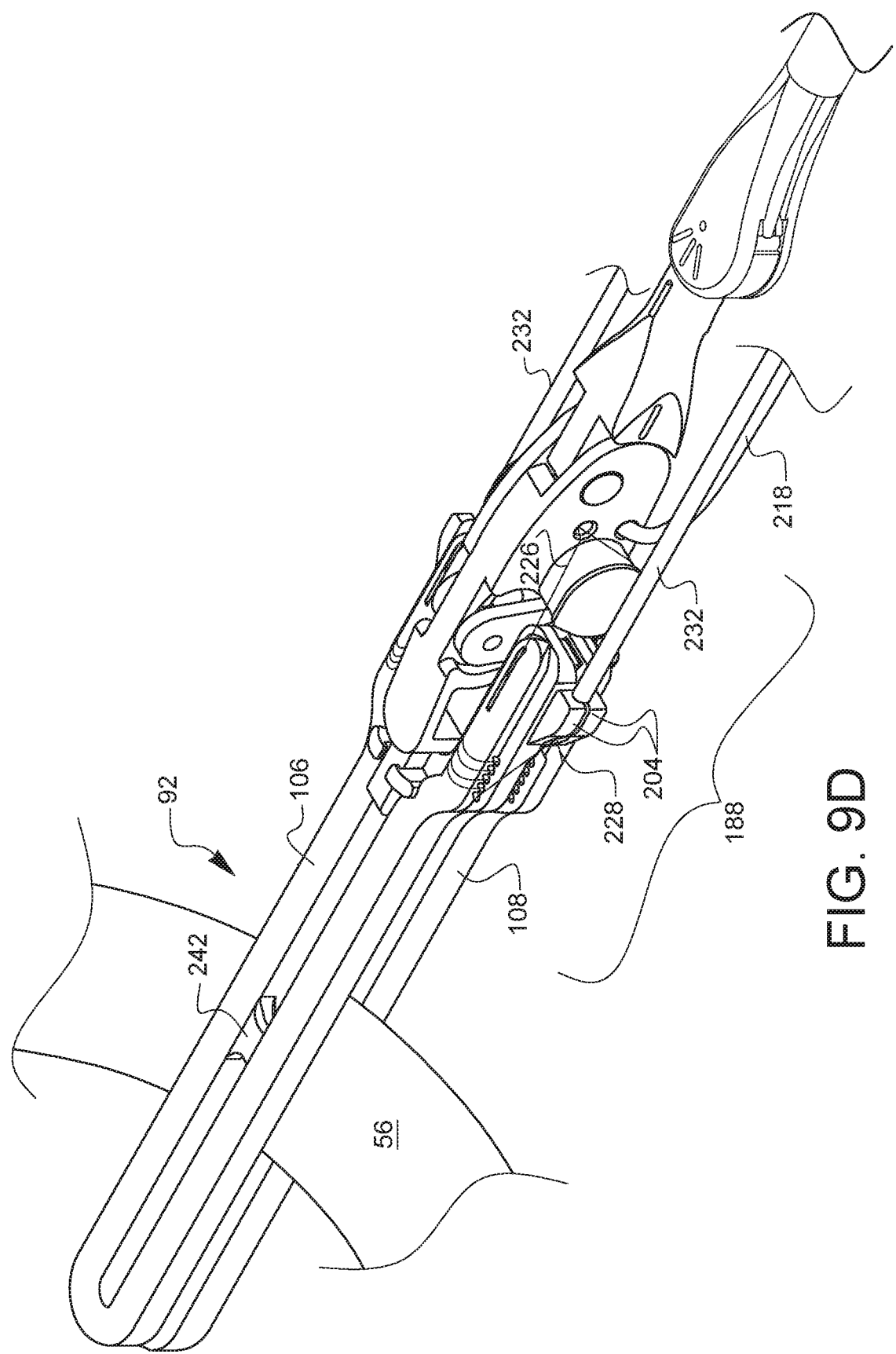
FIG. 9D is a perspective view of the surgical clamping device from inside a body cavity illustrating the resulting state of the clamping end after the procedure shown in FIG. 9C, in a tightened and clamped or closed position.
Figure 9E:
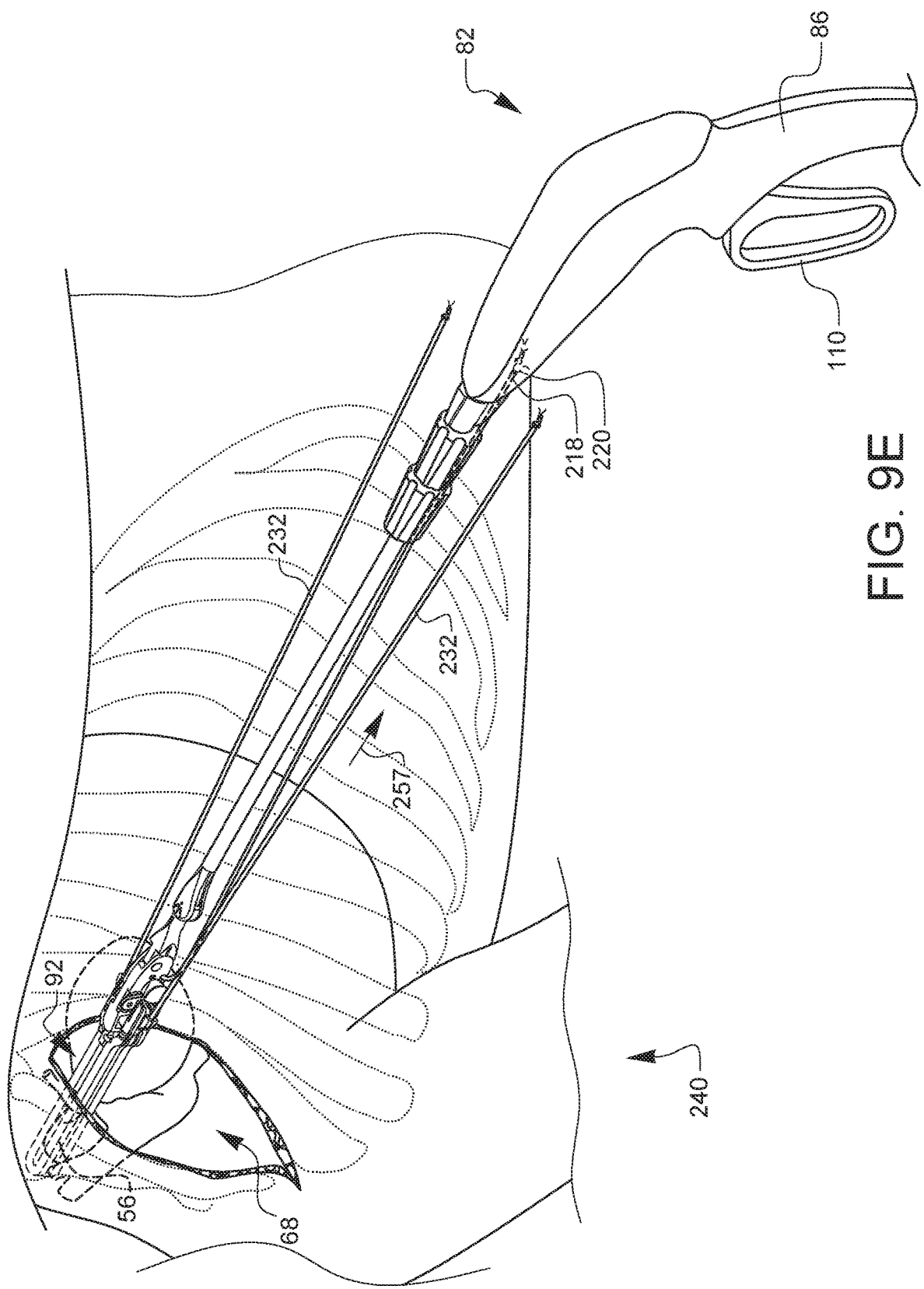
FIG. 9E is a perspective view of the surgical clamping device of FIG. 3A from outside a body cavity illustrating the removal of a release suture.

FIG. 9D is a perspective view of the surgical clamping device from inside a body cavity illustrating the resulting state of the clamping end after the procedure shown in FIG. 9C. In this view, the clamping jaws 106, 108 remain in a closed position and the corset sutures 228 are tightened as described in regard to FIG. 9C. It should be noted that the clamping end 92 of the surgical clamping device 82 still has the tightened corset sutures 228 constrained within the corset suture tubes 232, and the corset suture tubes 232 are held in the mating corset suture tube guides 204 on either clamp jaw 106, 108 and the release suture tube 218 and release suture 226 still hold the clamping end onto the actuator end 188 of the surgical clamping device 82. FIG. 9E is a perspective view of the surgical clamping device of FIG. 3A from outside a body cavity illustrating the removal of a release suture. FIG. 9E shows the severed end of the release suture tube 218 with the release suture ends 220 protruding from the end of the tube 218. Once the release suture tube 218 and the release suture 226, held within the release suture tube 218 have been severed, one suture end 220 and the release suture tube 218 can be grasped by the user and pulled in a direction 257 in order to fully remove both the release suture 226 and the release suture tube 218 from the clamping end 92 of the surgical clamping device 82. While the suture ends must be severed if held in place by a permanent mechanical fastener, other methods of securing the release suture and the release suture tubes do not require severing, but simply a reversal of the securing method as appropriate.

Figure 9F:
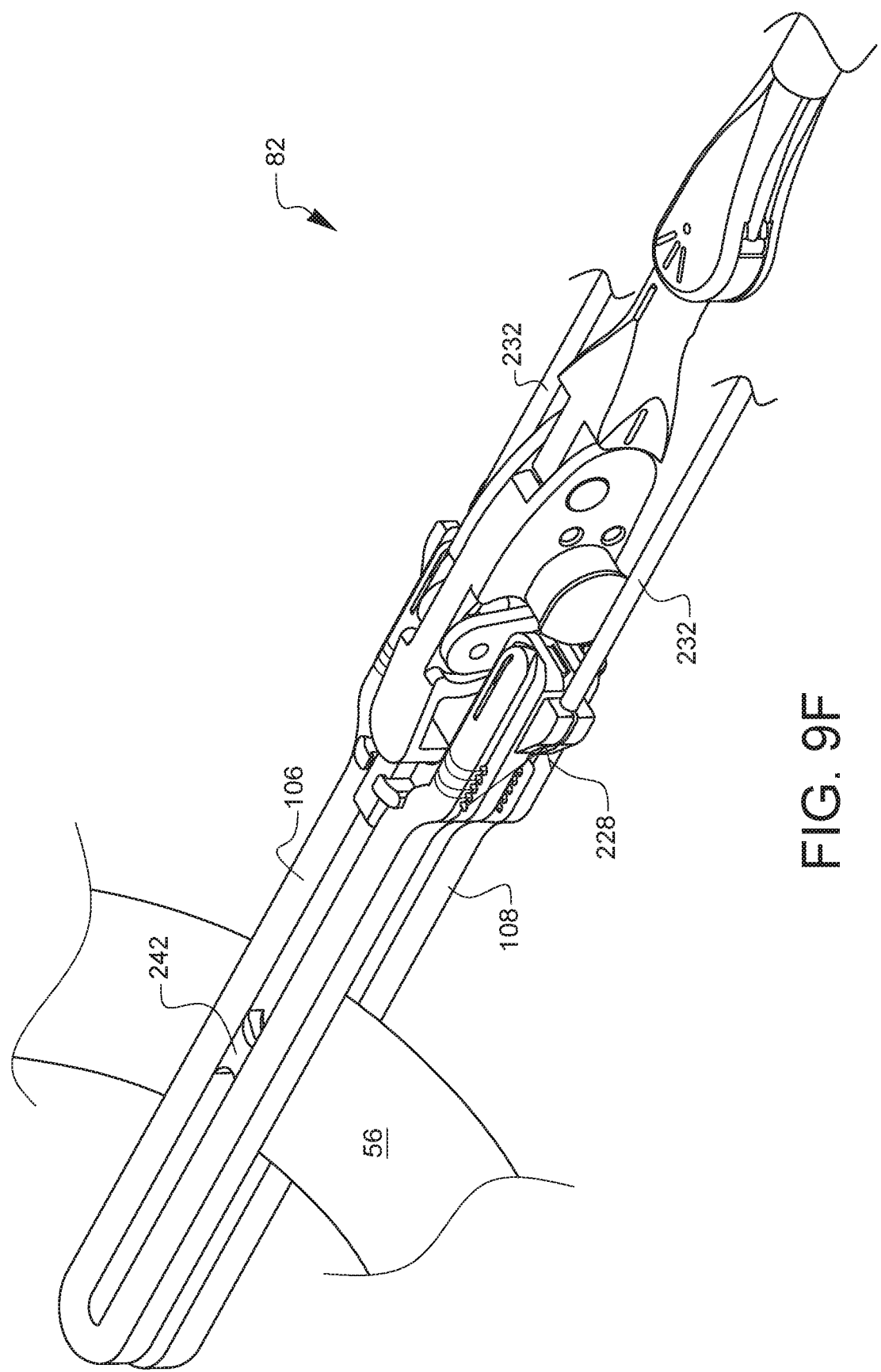
FIG. 9F is a perspective view of the surgical clamping device from inside a body cavity illustrating the resulting state of the clamping end after the procedure shown in FIG. 9E, in a released and locked and clamped or closed position.
Figure 9G:
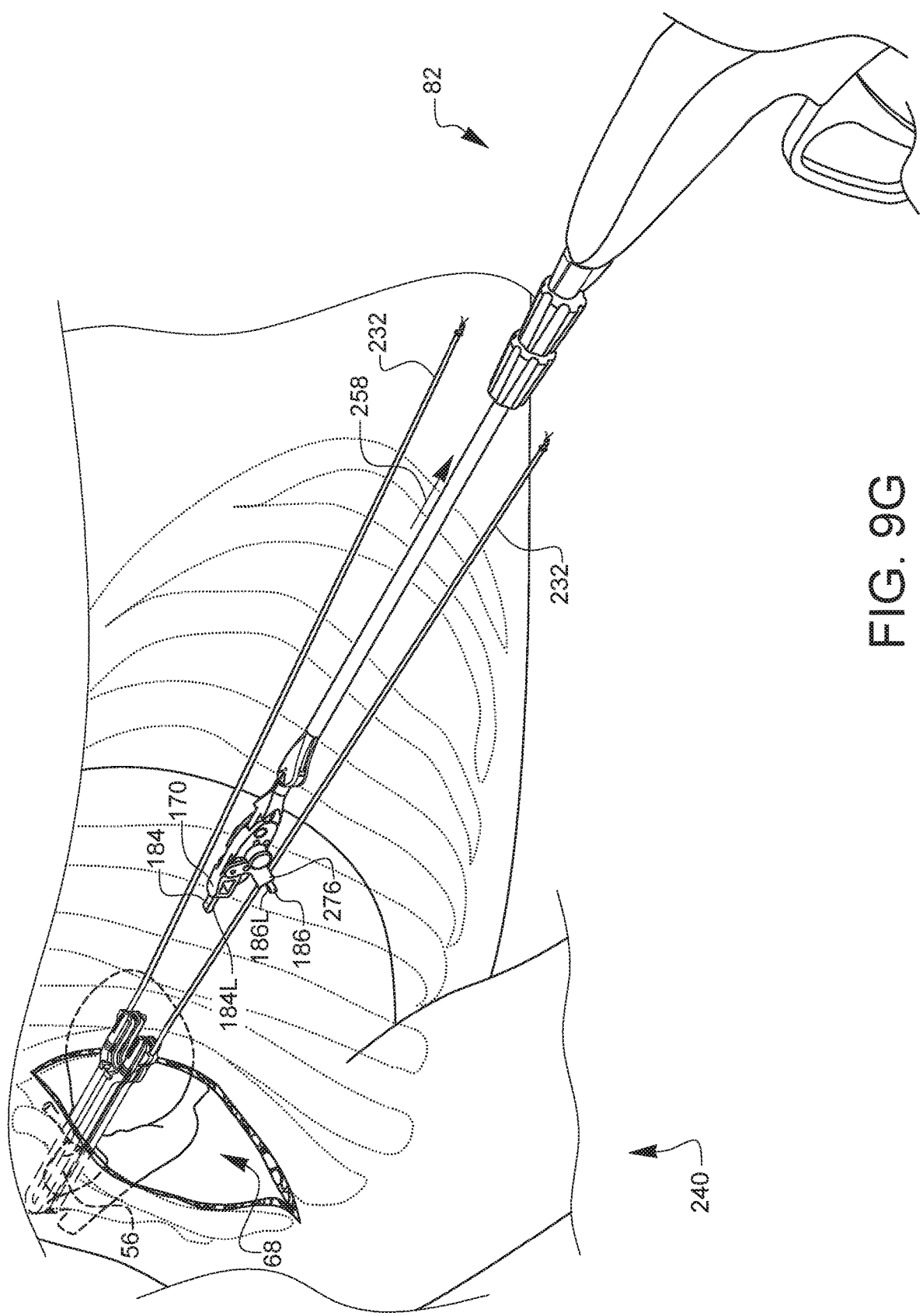
FIG. 9G is a perspective view of the surgical clamping device of FIG. 3A from outside a body cavity illustrating the separation of the clamping end from the actuator end.

FIG. 9F is a perspective view of the surgical clamping device from inside a body cavity illustrating the resulting state of the clamping end after the procedure shown in FIG. 9E. In this view, the clamping jaws 106, 108 remain in a closed position, the corset sutures 228 are tightened, and the release suture 226 has been removed as described in regard to FIG. 9E. FIG. 9G is a perspective view of the surgical clamping device of FIG. 3A from outside a body cavity illustrating the separation of the clamping end from the actuator end. As illustrated in FIG. 9G, the actuator lever 110 is released in direction 260 away from the handle 86 on the surgical clamping device 82. The release of the handle 86 by the operator allows the mobile finger 176 and the fixed finger 170 to separate enough to allow for the finger tab latch 186L of the finger tab 186 on the mobile finger 176 and the finger tab latch 184L of the finger tab 184 on the fixed finger 170 to both clear the distal end 194D of the strut 194 on both clamping jaws 106, 108. Once the latches 184L, 186L are clear of the distal end 194D of the strut 194, the minimally invasive surgical clamping device 82 is moved in direction 258 and removed from the surgical site and the minimally invasive opening 68 in the patient 240. This configuration and operation of the latches 184L, 186L has previously been described in further detail with regard to FIG. 4G, FIGS. 6A-6B, and FIGS. 7A-7B. At this stage, the clamping pressure on the aortic cross-clamp is still maintained by the secured corset suture tubes 232 and the corset suture 228 within on both sides of the first and second clamp jaws 106, 108.

FIG. 9H is a perspective view of the surgical clamping device of FIG. 3A in a separated and locked and clamped or closed position. This shows an enlarged view of the actuator end 188 end being separated by moving in direction 258 and removing the actuator end 188 from the clamping end 92 as described in regard to FIG. 9G. The complete removal of the release suture 226 shown in FIGS. 9E and 9F allows the separation or disengagement or detachment of the actuator end 188 of the surgical clamping device 82 from the clamping end 92 while leaving the clamping end 92 in a cross-clamp position on the aorta 56 within the patient 240 with clamping pressure maintained. This separation provides an effective means of providing cross-clamp pressure while preserving valuable space in and around a minimally invasive surgical opening 68 for other surgical tools necessary for surgical procedures for the duration of a minimally invasive surgical procedure. Upon completion of the minimally invasive surgical procedure, or at the end of the desired cross-clamp portion of the surgical procedure, the actuator end 188 may be reintroduced into the actuator interface 196 on each of the clamping jaws 106, 108 with the lever 110 partially squeezed. Once the actuator end 188 is slidably engaged into the clamping jaws 106, 108, the corset sutures 228 and the corset suture tubes 232 can be severed and removed from the clamping jaws 106, 108. The removal of the corset sutures 228 from the clamping jaws 106, 108 will now allow the clamping jaws 106, 108 to be separated and removed by opening the clamping jaws 106, 108 by fully releasing the actuation lever 110 on the surgical clamping device 82. Finally, the entire minimally invasive surgical clamping device 82 can be removed from the patient 240.

FIG. 10A is a bottom-right perspective view of a clamping jaw of the surgical clamping device of FIG. 3A. FIG. 10B is a top-right perspective view of a clamping jaw of the surgical clamping device of FIG. 3A. These figures describe the clamping jaw 106 in greater detail. The clamping jaw 106 defines two beams 262 coupled to a central strut 194. The two beams 262 define a clamping surface 282, are coupled to the strut 194 and terminate in a rounded distal end 106D. The positional indicator 242 joins the two beams 262 at their approximate midpoint. The positional indicator 242 may provide both structural support for the clamping jaw 106 as well a visual indication of position for a member of a surgical team during a minimal invasive surgical procedure. Near the proximal end 106P of the clamping jaw 106 are several inner corset suture channels 200, several outer corset suture channels 198, and corset suture tube guides 204 configured to receive sutures and suture tube guides as described previously in regard to FIGS. 5E and 5F.

The proximal end 106P of the clamping jaw 106 also includes several interlocking features configured for releasable pivoting when the clamp jaw 106 is paired with an identical clamp jaw 106 as shown in the embodiment first described in FIG. 3A and elsewhere herein. Each feature at the proximal end 106P of the clamping jaw corresponds with a mating part on an identical clamping jaw 106 that would be releasably and pivotably coupled to one another in an exemplary embodiment of the surgical clamping device as described herein. The clamp jaw includes a pivot 264 matched with a corresponding pivot recess 268 and a large alignment recess 266 matched with a large alignment tab 270. The clamp jaw 106 also includes a small alignment tab 276 matched with a corresponding small alignment recess 274, both of which have a release channel hole 272 in communication with a release channel 202 on the opposite side of the clamping jaw 106, further comprising one or more interlocking recesses configured for releasable pivoting.

The clamp jaw 106 also includes two finger tab guides 192 that define an actuator interface 196 or alignment guide configured for aligning and receiving an actuator interface 188 as described previously. The finger tab guides 192 which define the alignment guides or actuator interfaces for the clamping jaw 106 are located over the central strut 194, which has a distal end 194D and a proximal end 194P, the distal end 194D of the strut 194 is configured to receive and releasably hold one or more finger tab latches 184L, 186L as previously described. It should be noted that variations of these features in the clamp jaw 106 may also be used, such as varying numbers or shapes of corset suture channels, alternate arrangements and shapes of release channels, and other means of releasable pivoting may be known to those skilled in the art and employed in surgical clamping devices. Clamping jaws as described herein may be fabricated out of a variety of materials including metals, alloys, polymers or filled polymers. For example, the clamping jaws can be forged or milled from stainless steel or other metals commonly used in medical devices. Additionally, clamping jaws may be molded from materials such as polymers such as polyarylamide and other known moldable polymers, or glass or glass fiber filled polymers to provide a specific appearance or additional physical properties as desired. Other reinforcing fillers known to those skilled in the art may also be used.

Figure 10C:
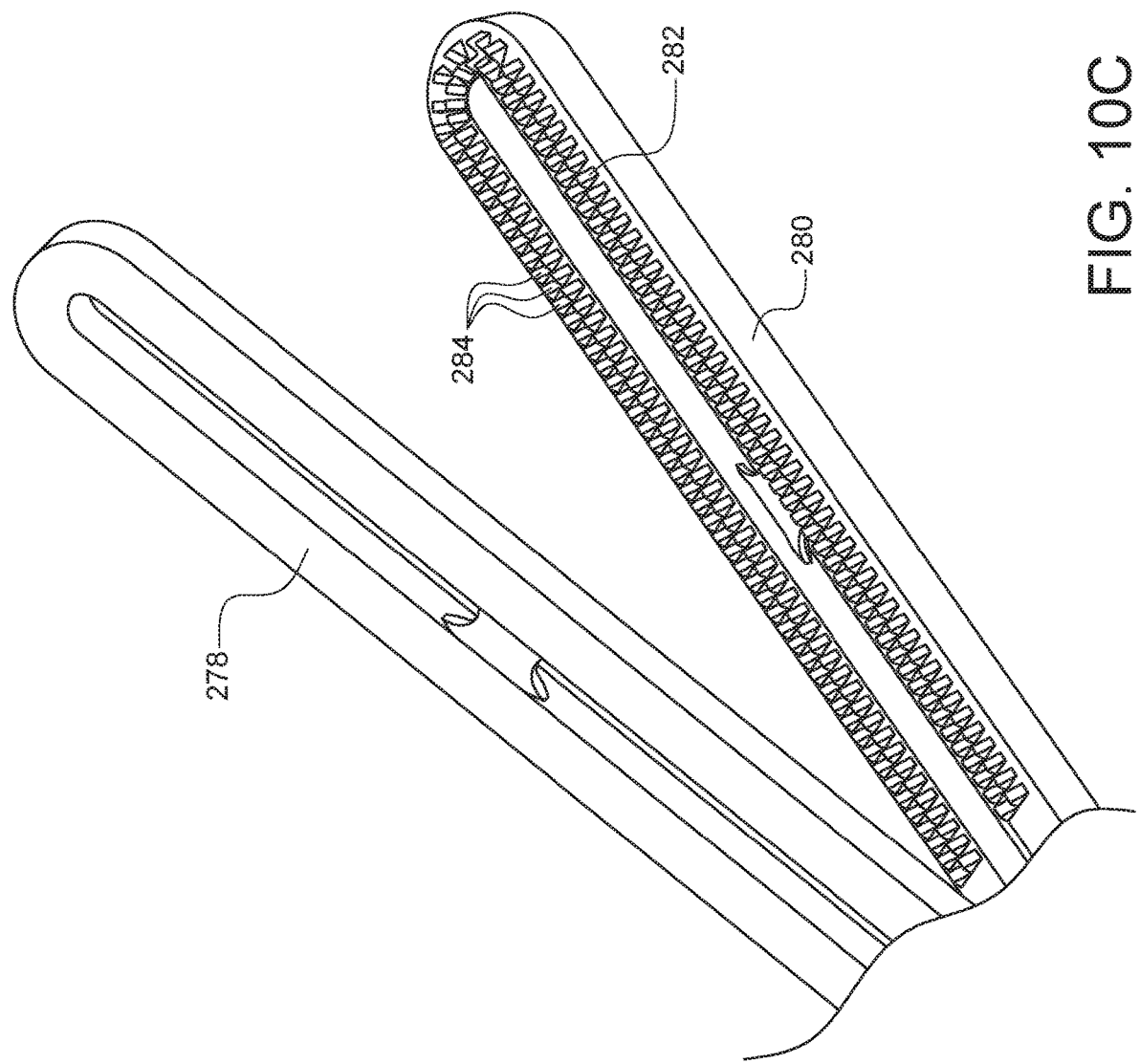
FIG. 10C is an enlarged top-right perspective view of an embodiment of the clamping jaws of FIGS. 10A and 10B illustrating a clamping surface having a resilient grip.

FIG. 10C is an enlarged top-right perspective view of an alternate embodiment of the clamping jaws of FIGS. 10A and 10B illustrating a clamping surface having a resilient grip. This embodiment of a first clamping jaw 278 and second clamping jaw 280 illustrate a clamping surface 282 having a resilient grip. The structural features 284 illustrated in FIG. 10C are designed and configured to provide a resilient, yet atraumatic grip during procedures requiring tissue occlusion. These types of features 284 avoid or reduce tissue damage during manipulation during various cardiac and other surgical procedures. Additional embodiments of physical or structural features 284 may include an intermeshing resilient grip or patterns such as Debakey, Bailey, Beck, Diethrich, Glover, Cooley, Gregory, Kay, and the like, which are known to those skilled in the art. Additionally, the clamping surface 282 could be covered, coated with, or surfaced with an elastomeric or plastic cushioning material, designed to reduce trauma and tissue damage during clamping. The clamping surface could also be comprised of a combination of physical and alternate surface material compositions as well as other well-known means of providing clamping surfaces with a resilient grip, atraumatic grip, or both.

Figure 11:
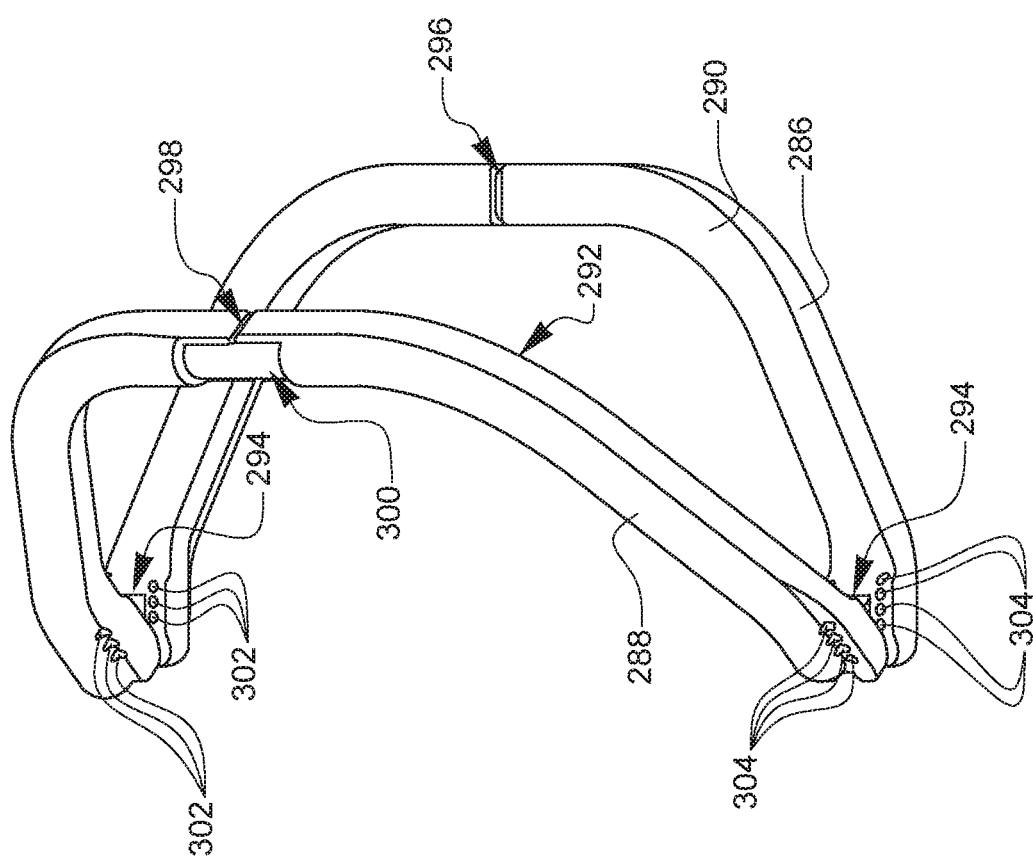
FIG. 11 is a perspective view of an alternate embodiment of a pair of clamping jaws.

FIG. 11 is a perspective view of an alternate embodiment of a pair of clamping jaws. This embodiment of clamping jaws is configured in such a geometry that allows for two clamping points across an aorta or blood vessel, thus impeding or ceasing blood flow from two locations when clamped. This clamping configuration may allow for surgical access to a short section of an aorta or blood vessel without the flow of blood through the vessel from either direction while clamped. The first clamping jaw 286 defines a clamping surface 290 and several interlocking features 294, and the second clamping jaw 288 also defines a clamping surface 292 and several interlocking features 294. The interlocking features 294 are similar to the pivot matched with a corresponding pivot recess and a large alignment recess matched with a large alignment tab as described previously in regard to the clamping jaw embodiments illustrated in FIGS. 10 and 10B. The clamping jaws 286, 288 also include small alignment tabs matched with corresponding small alignment recesses. The pivots, large and small alignment recesses, and large and small alignment tabs in this embodiment are simply noted as interlocking features 294 in FIG. 11. The interlocking features 294 are configured for releasable pivoting of the two clamping jaws 286, 288. Near the interlocking features 294, the clamping jaws 286, 288 further define suture recesses 296, 298 and an introducer recess 300 shown on second clamping jaw 288. There is a corresponding introducer recess on the second clamping jaw 286, not visible in this view. The introducer recesses 300 on both clamping jaws 286, 288 are configured for detachable or releasable coupling with a pair of corresponding pivotable and articulated introducer arms (not shown here). These introducer arms would be used in a similar configuration as the fixed finger and mobile finger as described previously. The suture recesses 296, 298 are configured to receive suture, which is used to secure and retain the clamping jaws 286, 288 onto the introducer arms (not shown in this view) until the introducer arms are released from the clamping jaws 286, 288. Also, in proximity to the interlocking features 294, the clamping jaws 286, 288 further define inner corset suture channels 302 and outer corset suture channels 304 configured to receive sutures which may be constrained within suture tube guides as described previously in regard to FIGS. 5E and 5F. These corset sutures are configured to secure the clamping jaws once placed over an aorta or blood vessel. While this embodiment shows identical clamping jaws which are configured to be pivotably mated, other embodiments may be made of non-identical clamping jaws, and may be pivotably mated or hinged by alternate means known to those skilled in the art.

It should be noted that variations of these features in the clamping jaws 286, 288 may also be used, such as varying numbers or shapes of corset suture channels and other means of releasable pivoting may be known to those skilled in the art and employed in surgical clamping devices. Clamping jaws as described herein may be fabricated out of a variety of materials including metals, alloys, polymers or filled polymers. For example, the clamping jaws can be forged or milled from stainless steel or other metals commonly used in medical devices. Additionally, clamping jaws may be molded from materials such as polymers such as polyarylamide and other known moldable polymers, or glass or glass fiber filled polymers to provide a specific appearance or additional physical properties as desired. Other reinforcing fillers known to those skilled in the art may also be used.

As an experimental example measuring clamping pressure, a porcine aorta was clamped utilizing an embodiment of the present disclosure. A porcine aorta was fastened to a peristaltic pump configured to pulse once per second, approximating a pulse rate for a human. A surgical clamping device was applied to the porcine aorta in accordance with the procedure and instrumentation described in regard to FIGS. 9A-9H. During the experiment, pressure was measured to be consistently held at 90 mm Hg for 3 hours, indicating a sufficient clamping pressure for the intended use of the surgical clamping device.

Embodiments of the surgical clamp device discussed herein, and their equivalents, may be advantageously used as an aortic cross clamp. An advantage of the embodiment described herein is that the impact to a limited access surgical access site is minimal, enabling surgeons to have more access for tools and other implements during a related surgical procedure. Furthermore, the articulating introducer shaft does not need to be reattached in order to remove the clamp when finished.

It should be understood that the term "suture", as used herein, is intended to cover any thread, cable, wire, filament, strand, line, yarn, gut, or similar structure, whether natural and/or synthetic, in monofilament, composite filament, or multifilament form (whether braided, woven, twisted, or otherwise held together), as well as equivalents, substitutions, combinations, and pluralities thereof for such materials and structures.

Various advantages of a minimally invasive surgical clamping device and methods for its use have been discussed above. Embodiments discussed herein have been described by way of example in this specification. It will be apparent to those skilled in the art that the forgoing detailed disclosure is intended to be presented by way of example only and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. As just one example, although mechanical knots have been discussed as examples of knotting to hold the first and second clamp jaws in a clamped position, it should be understood that any type of knot or fastening device, including knots tied by hand, forceps, or other manipulator directly into the suture can provide a suitable knotting. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A surgical device, comprising:
   a shaft having a proximal end and a distal end;
   an actuator assembly coupled to the distal end of the shaft, the actuator assembly comprising a fixed finger and a mobile finger, wherein the mobile finger is pivotable relative to the fixed finger from a first open position to a second fully closed position, and wherein an elongated finger tab is disposed at a distal end of each of the fixed finger and the mobile finger, and a latch is disposed at a distal end of each of the finger tabs;
   a clamping assembly comprising a first clamp jaw removably coupled to the mobile finger and a second clamp jaw removably coupled to the fixed finger such that the first clamp jaw and the second clamp jaw displace between an unclamped position and a clamped position when the mobile finger pivots relative to the fixed finger between the first position and the second position, each of the first clamp jaw and the second clamp jaw comprising:
   one or more channels; and
   a finger tab guide adapted to removably receive a corresponding one of the finger tabs, wherein the latch of each of the corresponding finger tabs engages a corresponding engagement portion of each of the first clamp jaw and the second clamp jaw to secure the finger tab within the finger tab guide, wherein when the first clamp jaw and the second clamp jaw are in the clamped position, the mobile finger is displaceable to an intermediate third position relative to the fixed finger such that the latch of each of the finger tabs is removable from the corresponding engagement portion of each of the first clamp jaw and the second clamp jaw and the finger tab may be removed from the finger tab guide as the shaft is moved proximally, thereby completely decoupling the clamping assembly from the first clamp jaw and the second clamp jaw while the first clamp jaw and the second clamp jaw are in the clamped position.

2. The surgical device of claim 1, wherein the one or more channels are configured for receiving one or more sutures.

3. The surgical device of claim 2, wherein the one or more sutures are configured to be secured with a mechanical fastener to maintain a clamping pressure.

4. The surgical device of claim 3, wherein the clamping pressure is maintained from about 10 mm Hg to about 125 mm Hg for about 0.1 hours to about 4 hours.

5. The surgical device of claim 1, wherein at least one of the one or more channels is configured to receive suture for releasably securing at least one of the first clamp jaw or the second clamp jaw to the actuator assembly.

6. The surgical device of claim 1, wherein the first clamp jaw is identical to the second clamp jaw.

7. The surgical device of claim 1, wherein a suture used for holding the first and second clamp jaws onto the actuator assembly is configured to be secured with a fastener.

8. The surgical device of claim 1, wherein the first and second clamp jaws further comprise one or more beams branching from a central structural point of each of the first and second clamp jaws.

9. The surgical device of claim 8, wherein the engagement portion of each of the first clamp jaw and the second clamp jaw is a ledge formed by a portion of the central structural point of each of the first and second clamp jaws.

10. The surgical device of claim 1, wherein the first clamp jaw and the second clamp jaw have a surface having a resilient grip.

11. The surgical device of claim 10, wherein the resilient grip is an intermeshing resilient grip on the surface of the first clamp jaw and the second clamp jaw.

12. The surgical device of claim 1, wherein at least one of the first or second clamp jaws further comprises a material selected from the group consisting of a metal, an alloy, a polymer and a filled polymer.

13. The surgical device of claim 12, wherein at least one of the first and second clamp jaws is comprised of a polyarylamide filled with glass fiber.

14. The surgical device of claim 1, further comprising:
    a housing; and
    an actuation lever pivotably coupled to a first portion of the housing, wherein the proximal end of the shaft is coupled to a second portion of the housing, and wherein the actuation lever is operatively coupled to the actuator assembly such that displacing the actuation lever relative to the housing pivots the mobile finger relative to the fixed finger from the first position to the second position.

* * * * *